United States Patent [19]
Thompson

[11] Patent Number: 5,902,880
[45] Date of Patent: May 11, 1999

[54] RNA POLYMERASE III-BASED EXPRESSION OF THERAPEUTIC RNAS

[75] Inventor: James Thompson, Boulder, Colo.

[73] Assignee: Ribozyme Pharmaceuticals, Inc., Boulder, Colo.

[21] Appl. No.: 08/337,608

[22] Filed: Nov. 10, 1994

Related U.S. Application Data

[63] Continuation-in-part of application No. 08/293,520, Aug. 19, 1994, abandoned.

[51] Int. Cl.$^6$ .............................. C12N 15/00; A61K 48/00
[52] U.S. Cl. ........................ 536/24.5; 536/23.1; 536/24.2; 536/24.33; 435/172.3; 514/44
[58] Field of Search .................................. 536/22.1, 23.1, 536/22.2, 24.1, 25.1, 91.25; 514/44, 2; 435/172.3, 320.1

[56] References Cited

U.S. PATENT DOCUMENTS

| | | | |
|---|---|---|---|
| 5,208,149 | 5/1993 | Inoaye | 435/172.3 |
| 5,324,643 | 6/1994 | Greatbatch et al. | 435/91.32 |

FOREIGN PATENT DOCUMENTS

| | | |
|---|---|---|
| 8911539 | 11/1989 | WIPO . |
| 9013641 | 11/1990 | WIPO . |
| 9207065 | 4/1992 | WIPO . |
| 9402595 | 2/1994 | WIPO . |

OTHER PUBLICATIONS

Adeniyi–Jones et al., "Generation of long read–through transcripts in vivo and in vitro by deletion 3' termination and processing sequences in the human tRNA$_i^{met}$ gene," *Nucleic Acids Research* 12:1101–1115 (1984).

Bredow et al., "Sequence and factor requirements for faithful in vitro transcription of human 7SL DNA," *Gene* 86:217–225 (1990).

Cech, "Ribozymes and Their Medical Implications," *JAMA* 260:3030–3034 (1988).

Cotten and Birnstiel, "Ribozyme Mediated Destruction of RNA in vivo," *EMBO J* 8:3861–3866 (1989).

Eguchi et al., "Antisense RNA$^1$," *Ann. Rev. Biochem.* 60:631–652 (1991).

Fowlkes and Shenk, "Transcriptional Control Regions of the Adenovirus VAI RNA Gene," *Cell* 22:405–413 (1980).

Geiduschek and Tocchini–Valentini, "Transcription by RNA Polymerase III," *Ann. Rev. Biochem.* 57:873–914 (1988).

Gupta and Reddy, "Compilation of small RNA sequences," *Nucleic Acids Research* 19:2073–2075 (1991).

Hall et al., "Transcription Initiation of Eucaryotic Transfer RNA Genes," *Cell* 29:3–5 (1982).

Howe and Shu, "Epstein–Barr Virus Small RNA (EBER) Genes: Unique Transcription Units That Combine RNA Polymerase II and III Promoter Elements," *Cell* 57:825–834 (1989).

Kickhoefer et al., "Vault Ribonucleoprotein Particles from Rat and Bullfrog Contain a Related Small RNA That Is Transcribed by RNA Polymerase III," *J. Biol. Chem.* 268:7868–7873 (1993).

Lee et al., "Transcription of Xenopus Selenocysteine tRNA$^{Ser}$ (Formerly Designated Opal Suppressor Phosphoserine tRNA) Gene Is Directed by Multiple 5'–Extragenic Regulatory Elements," *J. Biol. Chem.* 264:9696–9702 (1989).

Marshall, Science, 269, 1995, 1050–1055.

Barinaga, Science, 262, 1993, 1512–1514.

Uhlmann et al., Chem. Reviews., 90(4), 1990, 544–584.

Sarvea et al., AIDS Res. Human Ret., 9(5), 1993, 483–487.

Cotten et al., EMBO J., 8, 1989, 3861–3866.

Yu et al., Proc. Nat. Acad. Sci, 90, 1993, 6340–6344.

Mattaj et al., "Changing the RNA Polymerase Specificity of U snRNA Gene Promoters," *Cell* 55:435–442 (1988).

Nielsen et al., "Transcription of human 5S rRNA genes is influenced by an upstream DNA sequence," *Nucleic Acids Research* 21:3631–3636 (1993).

Romero and Blackburn, "A Conserved Secondary Structure for Telomerase RNA," *Cell* 67:343–353 (1991).

Specht et al., "Compilation of 5S rRNA and 5S rRNA gene sequences," *Nucleic Acids Research* 19:2189–2191 (1991).

Sullenger et al., "Overexpression of TAR Sequences Renders Cells Resistant to Human Immunodeficiency Virus Replication," *Cell* 63:601–608 (1990).

Sullenger et al., "Expression of Chimeric tRNA–Driven Antisense Transcripts Renders NIH 3T3 Cells Highly Resistant to Moloney Murine Leukemia Virus Replication," *Molecular and Cellular Biology* 10:6512–6523 (1990).

Tsai, et al., "In vitro selection of an RNA epitope immunologically cross–reactive with a peptide," *Proc. Natl. Acad. Sci. USA* 89:8864–8868 (1992).

Willis, "RNA Polymerase III Genes, factors and transcriptional specificity," *Biochem* 212:1–11 (1993).

Ballantyne et al., "Nucleotide sequence of the cDNA for murine intercellular adhesion molecule–1 (ICAM–1)," *Nucleic Acids Research* 17:5853 (1989).

Barinaga, "Ribozymes: Killing the Messenger," *Science* 262:1512–1514 (1993).

Cotten, "The in vivo application of ribozymes," *TIBTECH* 8:174–178 (1990).

Edgington, "Ribozymes: Stop Making Sense," *Biotechnology* 10:256–262 (1992).

Kita et al., "Sequence and expression of rat ICAM–1," *Biochem. Biophys. Acta* 1131:108–110 (1992).

Simons et al., "ICAM, an adhesion ligand of LFA–1, is homologous to the neutral cell adhesion molecule NCAM," *Nature* 331:624–627 (1988).

Usman and Cedergren, "Exploiting the chemical synthesis of RNA," *TIBS* 17:334–339 (1992).

*Primary Examiner*—Suzanne E. Ziska
*Assistant Examiner*—Andrew Milne
*Attorney, Agent, or Firm*—Lyon & Lyon LLP

[57] ABSTRACT

A transcribed non-naturally occuring RNA molecule comprising a desired RNA molecule, wherein the 3' region of the RNA is able to base-pair with at least 8 bases at the 5' terminus of the same RNA molecule.

24 Claims, 21 Drawing Sheets

FIG. 3.
VARIANTS OF Δ3-5 RNA
Δ3-5/HHI 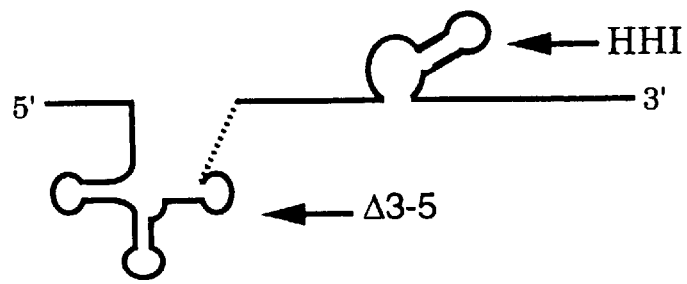
S3 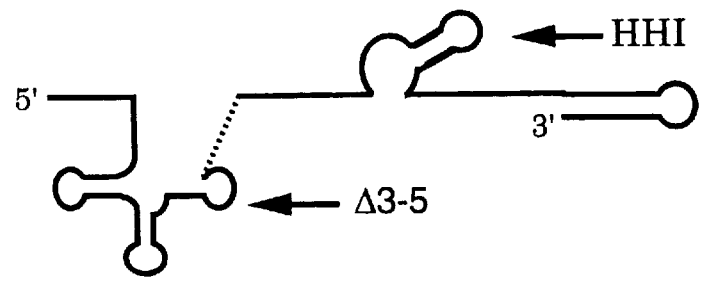
S5 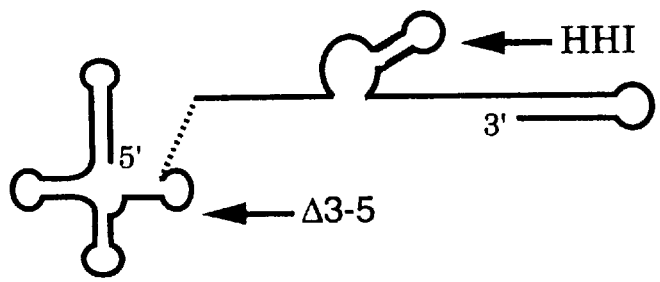
S35 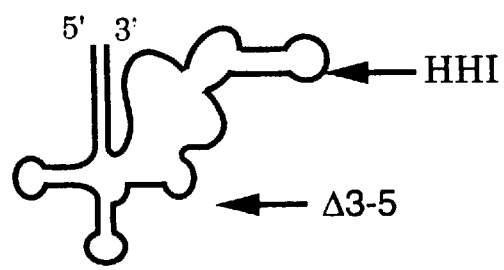
S35Plus 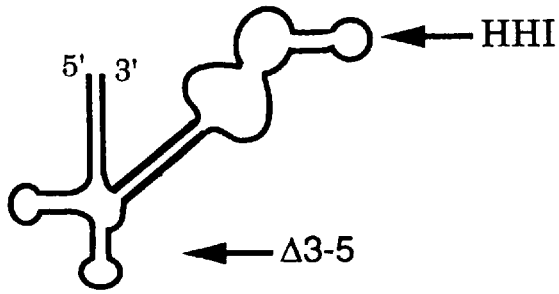

S35 tRNA Chimera (S35)

FIG. 11A  S35 Sequence

| | | | | |
|---|---|---|---|---|
| GGCAGAACAG | CAGAGUGGCG | CAGCGGAAGC | GUGCUGGGCC | CAUAACCCAG | 50 |
| AGGUCGAUGG | AUCGAAACCC | CGGAUCGUAC | CGCGGUGGAU | CCACUCUGCU | 100 |
| GUUCUGUUU | | | | | 109 |

FIG. 11B.  HHIS35

GGCAGAACAG CAGAGUGGCG CAGCGGAAGC GUGCUGGGCC CAUAACCCAG  50
AGGUCGAUGG AUCGAAACCC CGGAUCGUAC CGCGG<u>CACAA CACUGAUGAG</u>  100
<u>GACCGAAAGG UCCGAAACGG GCA</u>GGAUCCA CUCUGCUGUU CUGUUU  146

Underlined bases indicate the HHI ribozyme sequence

FIG. 12A.  S35 Plus Sequence

GGCAGAACAG CAGAGUGGCG CAGCGGAAGC GUGCUGGGCC CAUAACCCAG  50
AGGUCGAUGG AUCGAAACCC CGGAUCGUAC CGCGGGGAUC CUAACGAUCC  100
GGGGUGUCGA UCCAUCACUC UGCUGUUCUG UU U  133

FIG. 12B.  HHIS35 Plus

GGCAGAACAG CAGAGUGGCG CAGCGGAAGC GUGCUGGGCC CAUAACCCAG  50
AGGUCGAUGG AUCGAAACCC CGGAUCGUAC CGCGG<u>CACAA CACUGAUGAG</u>  100
<u>GACCGAAAGG UCCGAAACGG GCA</u>GGAUCCU AACGAUCCGG GGUGUCGAUC  150
CAUCACUCUG CUGUUCUGUU U  171

Underlined bases indicate the HHI ribozyme sequence

PROPOSED CHEMICAL FORMULA FOR S35 EXPRESSION CASSETTE

FIG. 13.

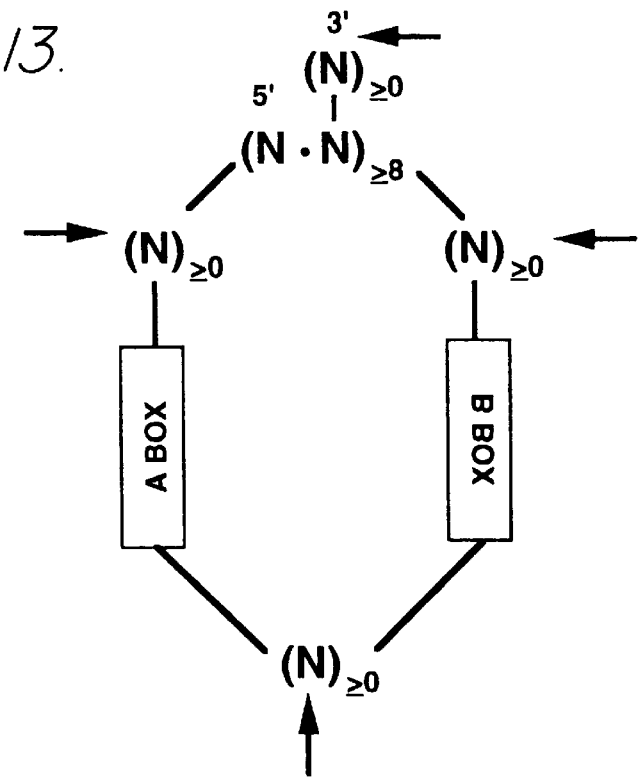

A BOX = URGCNNAGYGG

B BOX = GGUUCGANUCC

This is based on Geiduschek & Tocchini-Valentini, (1988) Annu. Review Biochem. 57, 873-914. However this consensus sequence is not meant to be limiting N = A, U, G, or C R = Purine Y = Pyrimidine

• = Indicates base-pairing

— = Indicates covalent linkage

➤ = Indicates sites at which desired RNAs can be cloned

FIG. 16.
TRZ tRNA CHIMERA
A: TRZ-A
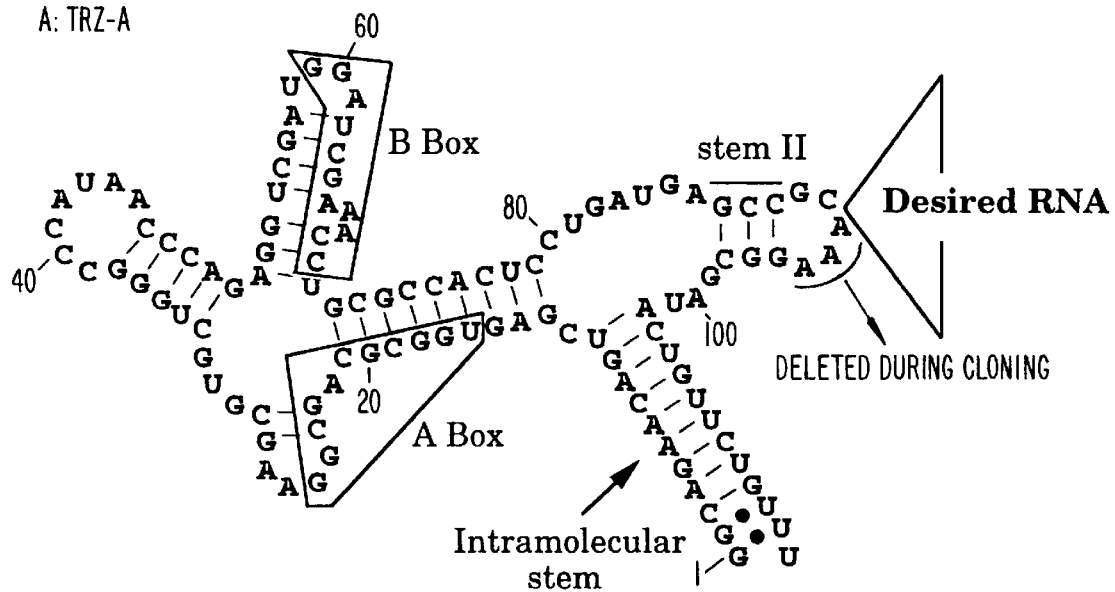
B: TRZ-B
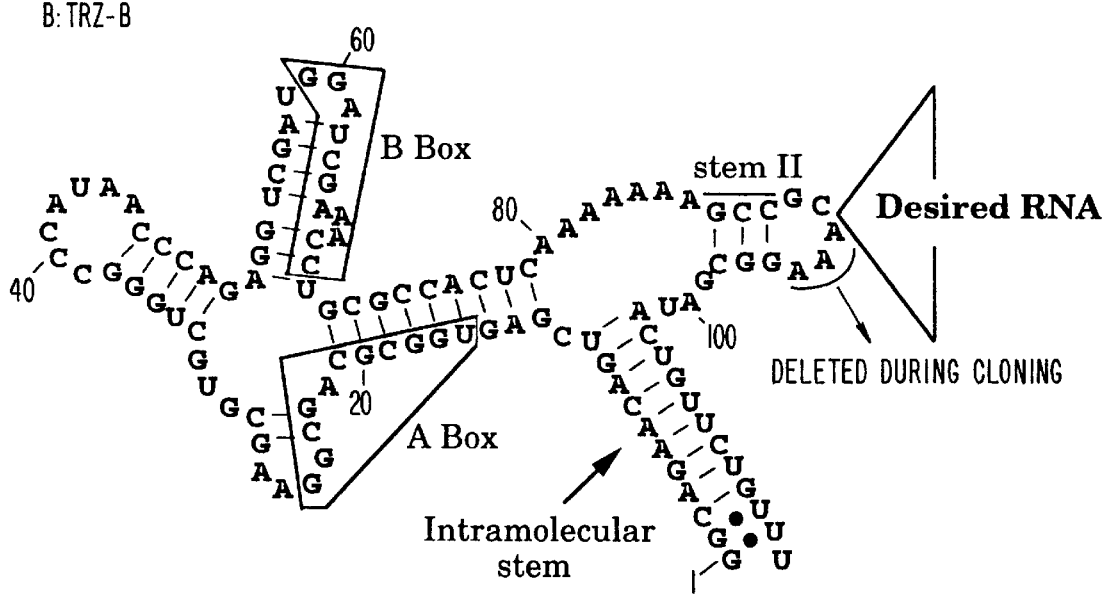

RNA POLYMERASE III-BASED EXPRESSION OF THERAPEUTIC RNAS

BACKGROUND OF THE INVENTION

This application is a continuation-in-part of James Thompson, "Improved RNA Polymerase III-Based Expression of Therapueitc RNAS", U.S. Ser. No. 08/293,520, filed Aug. 19, 1994 now abandoned, hereby incorporated by reference herein.

This invention relates to RNA polymerase III-based methods and systems for expression of therapeutic RNAs in cells in vivo or in vitro.

The RNA polymerase III (pol III) promoter is one found in DNA encoding 5S, U6, adenovirus VA1, Vault, telomerase RNA, tRNA genes, etc., and is transcribed by RNA polymerase III (for a review see Geiduschek and Tocchini-Valentini, 1988 Annu. Rev. Biochem. 57, 873–914; Willis, 1993 Eur. J. Biochem. 212, 1–11). There are three major types of pol III promoters types 1, 2 and 3 (Geiduschek and Tocchini-Valentini, 1988 supra; Willis, 1993 supra) (see FIG. 1). Type 1 pol III promoter consists of three cis-acting sequence elements downstream of the transcriptional start site a) 5'sequence element (A block); b) an intermediate sequence element (I block); c) 3' sequence element (C block). 5S ribosomal RNA genes are transcribed using the type 1 pol III promoter (Specht et al., 1991 Nucleic Acids Res. 19, 2189–2191.

The type 2 pol III promoter is characterized by the presence of two cis-acting sequence elements downstream of the transcription start site. All Transfer RNA (tRNA), adenovirus VA RNA and Vault RNA (Kikhoefer et al., 1993, J. Biol. Chem. 268, 7868–7873) genes are transcribed using this promoter (Geiduschek and Tocchini-Valentini, 1988 supra; Willis, 1993 supra). The sequence composition and orientation of the two cis-acting sequence elements- A box (5' sequence element) and B box (3' sequence element) are essential for optimal transcription by RNA polymerase III.

The type 3 pol III promoter contains all of the cis-acting promoter elements upstream of the transcription start site. Upstream sequence elements include a traditional TATA box (Mattaj et al., 1988 Cell 55, 435– 442), proximal sequence element (PSE) and a distal sequence element (DSE; Gupta and Reddy, 1991 Nucleic Acids Res. 19, 2073–2075). Examples of genes under the control of the type 3 pol III promoter are U6 small nuclear RNA (U6 snRNA) and Telomerase RNA genes.

In addition to the three predominant types of pol III promoters described above, several other pol III promoter elements have been reported (Willis, 1993 supra) (see FIG. 1). Epstein-Barr-virus-encoded RNAs (EBER), Xenopus seleno-cysteine tRNA and human 7SL RNA are examples of genes that are under the control of pol III promoters distinct from the aforementioned types of promoters. EBER genes contain a functional A and B box (similar to type 2 pol III promoter). In addition they also require an EBER-specific TATA box and binding sites for ATF transcription factors (Howe and Shu, 1989 Cell 57, 825–834). The seleno-cysteine tRNA gene contains a TATA box, PSE and DSE (similar to type 3 pol III promoter). Unlike most tRNA genes, the seleno-cysteine tRNA gene lacks a functional A box sequence element. It does require a functional B box (Lee et al., 1989 J. Biol. Chem. 264, 9696–9702). The human 7SL RNA gene contains an unique sequence element downstream of the transcriptional start site. Additionally, upstream of the transcriptional start site, the 7SL gene contains binding sites for ATF class of transcription factors and a DSE (Bredow et al., 1989 Gene 86, 217–225).

Gilboa WO 89/11539 and Gilboa and Sullenger WO 90/13641 describe transformation of eucaryotic cells with DNA under the control of a pol III promoter. They state:

"In an attempt to improve antisense RNA synthesis using stable gene transfer protocols, the use of pol III promoters to drive the expression of antisense RNA can be considered. The underlying rationale for the use of pol III promoters is that they can generate substantially higher levels of RNA transcripts in cells as compared to pol II promoters. For example, it is estimated that in a eucaryotic cell there are about $6 \times 10^7$ t-RNA molecules and $7 \times 10^5$ mRNA molecules, i.e., about 100 fold more pol III transcripts of this class than total pol II transcripts. Since there are about 100 active t-RNA genes per cell, each t-RNA gene will generate on the average RNA transcripts equal in number to total pol II transcripts. Since an abundant pol II gene transcript represents about 1% of total mRNA while an average pol II transcript represents about 0.01% of total mRNA, a t-RNA (pol III) based transcriptional unit may be able to generate 100 fold to 10,000 fold more RNA than a pol II based transcriptional unit. Several reports have described the use of pol III promoters to express RNA in eucaryotic cells. Lewis and Manley and Sisodia have fused the Adenovirus VA-1 promoter to various DNA sequences (the herpes TK gene, globin and tubulin) and used transfection protocols to transfer the resulting DNA constructs into cultured cells which resulted in transient synthesis of RNA in the transduced cell. De la Pena and Zasloff have expressed a t-RNA-Herpes TK fusion DNA construct upon microinjection into frog oocytes. Jennings and Molloy have constructed an antisense RNA template by fusing the VA-1 gene promoter to a DNA fragment derived from SV40 based vector which also resulted in transient expression of antisense RNA and limited inhibition of the target gene". [Citations omitted.]

The authors describe a fusion product of a chimeric tRNA and an RNA product (see FIG. 1C of WO 90/13641). In particular they describe a human tRNA $met_j$ derivative 3-5. 3-5 was derived from a cloned human tRNA gene by deleting 19 nucleotides from the 3' end of the gene. The authors indicate that the truncated gene can be transcribed if a termination signal is provided, but that no processing of the 3' end of the RNA transcript takes place.

Adeniyi-Jones et al., 1984 Nucleic Acids Res. 12, 1101–1115, describe certain constructions which "may serve as the basis for utilizing the tRNA gene as a 'portable promoter' in engineered genetic constructions." The authors describe the production of a so-called Δ3'-5 in which 11 nucleotides of the 3'-end of the mature $tRNA_j^{met}$ sequence are replaced by a plasmid sequence, and are not processed to generate a mature tRNA. The authors state:

"the properties of the $tRNA_j^{met}$ 3' deletion plasmids described in this study suggest their potential use in certain engineered genetic constructions. The tRNA gene could be used to promote transcription of theoretically any DNA sequence fused to the 3' border of the gene, generating a fusion gene which would utilize the efficient polymerase III promoter of the human tRNA-$_j^{met}$ gene. By fusion of the DNA sequence to a $tRNA_j^{met}$ deletion mutant such as Δ3'-4, a long read-through transcript would be generated in vivo (dependent, of course, on the absence of effective RNA polymerase III termination sequences). Fusion of the DNA sequence to a $tRNA_j^{met}$ deletion mutant such as Δ3'-5 would lead to the generation of a co-transcript from which subsequent processing of the tRNA leader at the 5' portion of the fused transcript would be blocked. Control over processing may be of some biological use in engineered constructions, as suggested by properties of mRNA species bearing tRNA sequences as 5' leaders in prokaryotes. Such "dual transcripts" code for several predominant bacterial proteins such as EF-Tu and may use the tRNA leaders as a means of stabilizing the transcript from degradation in vivo. The potential use of the tRNA$_j^{met}$ gene as a "promoter leader" in eukaryotic systems has been realized recently in our laboratory. Fusion genes consisting of the deleted tRNA$_j^{met}$ sequences contained on plasmids Δ3'-4 and Δ3'-5 in front of a promoter-less Herpes simplex type I thymidine kinase gene yield viral-specific enzyme resulting from RNA polymerase III dependent transcription in both X. laevis oocytes and somatic cells". [References omitted].

Sullenger et al., 1990 Cell 63, 601–619, describe overexpression of TAR-containing sequences using a chimeric tRNA$_j^{met}$-TAR transcription unit in a double copy (DC) murine retroviral vector.

Sullenger et al., 1990 Molecular and Cellular Bio. 10, 6512, describe expression of chimeric tRNA driven antisense transcripts. It indicates:

"successful use of a tRNA-driven antisense RNA transcription system was dependent on the use of a particular type of retroviral vector, the double-copy (DC) vector, in which the chimeric tRNA gene was inserted in the viral LTR. The use of an RNA pol III-based transcription system to stably express high levels of foreign RNA sequences in cells may have other important applications. Foremost, it may significantly improve the ability to inhibit endogenous genes in eucaryotic cells for the study of gene expression and function, whether antisense RNA, ribozymes, or competitors of sequence-specific binding factors are used. tRNA-driven transcription systems may be particularly useful for introducing "mutations" into the germ line, i.e., for generating transgenic animals or transgenic plants. Since tRNA genes are ubiquitously expressed in all cell types, the chimeric tRNA genes may be properly expressed in all tissues of the animal, in contrast to the more idiosyncratic behavior of RNA pol II-based transcription units. However, homologous recombination represents a more elegant although, at present, very cumbersome approach for introducing mutations into the germ line. In either case, the ability to generate transgenic animals or plants carrying defined mutations will be an extremely valuable experimental tool for studying gene function in a developmental context and for generating animal models for human genetic disorders. In addition, tRNA-driven gene inhibition strategies may also be useful in creating pathogen-resistant livestock and plants." [References omitted.]

Cotten and Birnstiel, 1989 EMBO Jrnl. 8, 3861, describe the use of tRNA genes to increase intracellular levels of ribozymes. The authors indicate that the ribozyme coding sequences were placed between the A and the B box internal promoter sequences of the Xenopus tRNA$^{met}$ gene. They also indicate that the targeted hammerhead ribozymes were active in vivo.

SUMMARY OF THE INVENTION

Applicant has determined that the level of production of a foreign RNA, using a RNA polymerase III (pol III) based system, can be significantly enhanced by ensuring that the RNA is produced with the 5' terminus and a 3' region of the RNA molecule base-paired together to form a stable intramolecular stem structure. This stem structure is formed by hydrogen bond interactions (either Watson-Crick or non-Watson-Crick) between nucleotides in the 3' region (at least 8 bases) and complementary nucleotides in the 5' terminus of the same RNA molecule.

Although the example provided below involves a type 2 pol III gene unit, a number of other pol III promoter systems can also be used, for example, tRNA (Hall et al., 1982 Cell 29, 3–5), 5S RNA (Nielsen et al., 1993, Nucleic Acids Res. 21, 3631–3636), adenovirus VA RNA (Fowlkes and Shenk, 1980 Cell 22, 405–413), U6 snRNA (Gupta and Reddy, 1990 Nucleic Acids Res. 19, 2073–2075), vault RNA (Kickoefer et al., 1993 J. Biol. Chem. 268, 7868–7873), telomerase RNA (Romero and Blackburn, 1991 Cell 67, 343–353), and others.

The construct described in this invention is able to accumulate RNA to a significantly higher level than other constructs, even those in which 5' and 3' ends are involved in hairpin loops. Using such a construct the level of expression of a foreign RNA can be increased to between 20,000 and 50,000 copies per cell. This makes such constructs, and the vectors encoding such constructs, excellent for use in decoy, therapeutic editing and antisense protocols as well as for ribozyme formation. In addition, the molecules can be used as agonist or antagonist RNAs (affinity RNAs). Generally, applicant believes that the intramolecular base-paired interaction between the 5' terminus and the 3' region of the RNA should be in a double-stranded structure in order to achieve enhanced RNA accumulation.

Thus, in one preferred embodiment the invention features a pol III promoter system (e.g., a type 2 system) used to synthesize a chimeric RNA molecule which includes tRNA sequences and a desired RNA (e.g., a tRNA-based molecule).

The following exemplifies this invention with a type 2 pol III promoter and a tRNA gene. Specifically to illustrate the broad invention, the RNA molecule in the following example has an A box and a B box of the type 2 pol III promoter system and has a 5' terminus or region able to base-pair with at least 8 bases of a complementary 3' end or region of the same RNA molecule. This is meant to be a specific example. Those in the art will recognize that this is but one example, and other embodiments can be readily generated using other pol III promoter systems and techniques generally known in the art.

By "terminus" is meant the terminal bases of an RNA molecule, ending in a 3' hydroxyl or 5' phosphate or 5' cap moiety. By "region" is meant a stretch of bases 5' or 3' from the terminus that are involved in base-paired interactions. It need not be adjacent to the end of the RNA. Applicant has determined that base pairing of at least one end of the RNA molecule with a region not more than about 50 bases, and preferably only 20 bases, from the other end of the molecule provides a useful molecule able to be expressed at high levels.

By "3' region" is meant a stretch of bases 3' from the terminus that are involved in intramolecular bas-paired interaction with complementary nucleotides in the 5' terminus of the same molecule. The 3' region can be designed to include the 3' terminus. The 3' region therefore is ≧0 nucleotides from the 3' terminus. For example, in the S35 construct described in the present invention (FIG. 7) the 3' region is one nucleotide from the 3' terminus. In another example, the 3' region is ~43 nt from 3' terminus. These examples are not meant to be limiting. Those in the art will recognize that other embodiments can be readily generated using techniques generally known in the art. Generally, it is preferred to have the 3' region within 100 bases of the 3' terminus.

By "tRNA molecule" is meant a type 2 pol III driven RNA molecule that is generally derived from any recognized tRNA gene. Those in the art will recognize that DNA encoding such molecules is readily available and can be modified as desired to alter one or more bases within the DNA encoding the RNA molecule and/or the promoter system. Generally, but not always, such molecules include an A box and a B box that consist of sequences which are well known in the art (and examples of which can be found throughout the literature). These A and B boxes have a certain consensus sequence which is essential for a optimal pol III transcription.

By "chimeric tRNA molecule" is meant a RNA molecule that includes a pol III promoter (type 2) region. A chimeric tRNA molecule, for example, might contain an intramolecular base-paired structure between the 3' region and complementary 5' terminus of the molecule, and includes a foreign RNA sequence at any location within the molecule which does not affect the activity of the type 2 pol III promoter boxes. Thus, such a foreign RNA may be provided at the 3' end of the B box, or may be provided in between the A and the B box, with the B box moved to an appropriate location either within the foreign RNA or another location such that it is effective to provide pol III transcription. In one example, the RNA molecule may include a hammerhead ribozyme with the B box of a type 2 pol III promoter provided in stem II of the ribozyme. In a second example, the B box may be provided in stem IV region of a hairpin ribozyme. A specific example of such RNA molecules is provided below. Those in the art will recognize that this is but one example, and other embodiments can be readily generated using techniques generally known in the art.

By "desired RNA" molecule is meant any foreign RNA molecule which is useful from a therapeutic, diagnostic, or other viewpoint. Such molecules include antisense RNA molecules, decoy RNA molecules, enzymatic RNA, therapeutic editing RNA (Woolf and Stinchcomb, "Oligomer directed in situ reversion (ISR) of genetic mutations", filed Jul. 6, 1994, U.S. Ser. No. 08/271,280, hereby incorporated by reference) and agonist and antagonist RNA.

By "antisense RNA" is meant a non-enzymatic RNA molecule that binds to another RNA (target RNA) by means of RNA—RNA interactions and alters the activity of the target RNA (Eguchi et al., 1991 Annu. Rev. Biochem. 60, 631–652). By "enzymatic RNA" is meant an RNA molecule with enzymatic activity (Cech, 1988 J. American. Med. Assoc. 260, 3030–3035). Enzymatic nucleic acids (ribozymes) act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through base-pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990 Cell 63, 601–608). This is meant to be a specific example. Those in the art will recognize that this is but one example, and other embodiments can be readily generated using techniques generally known in the art.

By "therapeutic editing RNA" is meant an antisense RNA that can bind to its cellular target (RNA or DNA) and mediate the modification of a specific base (Woolf and Stinchcomb, supra).

By "agonist RNA" is meant an RNA molecule that can bind to protein receptors with high affinity and cause the stimulation of specific cellular pathways.

By "antagonist RNA" is meant an RNA molecule that can bind to cellular proteins and prevent it from performing its normal biological function (for example, see Tsai et al., 1992 Proc. Natl. Acad. Sci. USA 89, 8864–8868).

By "complementary" is meant a RNA sequence that can form hydrogen bond(s) with other RNA sequence by either traditional Watson-Crick or other non-traditional types (for example, Hoogsteen type) of base-pairing interaction.

In other aspects, the invention includes vectors encoding RNA molecules as described above, cells including such vectors, methods for producing the desired RNA, and use of the vectors and cells to produce this RNA.

By "vectors" is meant any nucleic acid- and/or viral-based technique used to deliver a desired nucleic acid.

Thus, the invention features a transcribed non-naturally occuring RNA molecule which includes a desired therapeutic RNA portion and an intramolecular stem formed by base-pairing interactions between a 3' region and complementary nucleotides at the 5' terminus in the RNA. The stem preferably includes at least 8 base pairs, but may have more, for example, 15 or 16 base pairs.

In preferred embodiments, the 5' terminus of the chimeric tRNA includes a portion of the precursor molecule of the primary tRNA molecule, of which ≧8 nucleotides are involved in base-pairing interaction with the 3' region; the chimeric tRNA contains A and B boxes; natural sequences 3' of the B box are deleted, which prevents endogenous RNA processing; the desired RNA molecule is at the 3' end of the B box; the desired RNA molecule is between the A and the B box; the desired RNA molecule includes the B box; the desired RNA molecule is selected from the group consisting of antisense RNA, decoy RNA, therapeutic editing RNA, enzymatic RNA, agonist RNA and antagonist RNA; the molecule has an intramolecular stem resulting from a base-paired interaction between the 5' terminus of the RNA and a complementary 3' region within the same RNA, and includes at least 8 bases; and the 5' terminus is able to base pair with at least 15 bases of the 3' region.

In most preferred embodiments, the molecule is transcribed by a RNA polymerase III based promoter system, e.g., a type 2 pol III promoter system; the molecule is a chimeric tRNA, and may have the A and B boxes of a type 2 pol III promoter separated by between 0 and 300 bases; DNA vector encoding the RNA molecule of claim 1.

In other related aspects, the invention features an RNA or DNA vector encoding the above RNA molecule, with the portions of the vector encoding the RNA functioning as a RNA pol III promoter; or a cell containing the vector; or a method to provide a desired RNA molecule in a cell, by introducing the molecule into a cell with an RNA molecule as described above. The cells can be derived from animals, plants or human beings.

Other features and advantages of the invention will be apparent from the following description of the preferred embodiments thereof, and from the claims.

DESCRIPTION OF THE PREFERRED EMBODIMENTS

The drawings will first briefly be described.

Drawings

FIG. 1. Schematic representation of RNA polymerse III promoter structure. Arrow indicates the transcription start site and the direction of coding region. A, B and C, refer to consensus A, B and C box promoter sequences. I, refers to intermediate cis-acting promoter sequence. PSE, refers to proximal sequence element. DSE, refers to distal sequence element. ATF, refers to activating transcription factor binding element. ?, refers to cis-acting sequence element that has not been fully characterized. EBER, Epstein-Barr-virus-encoded-RNA. TATA is a box well known in the art.

FIG. 2. Sequence of the primary $tRNA_j^{met}$ and Δ3-5 transcripts. The A and B box are internal promoter regions necessary for pol III transcription. Arrows indicate the sites of endogenous tRNA processing. The Δ3-5 transcript is a truncated version of tRNA wherein the sequence 3' of B box has been deleted (Adeniyi-Jones et al., 1984 supra). This modification renders the Δ3-5 RNA resistant to endogenous tRNA processing.

FIG. 3. Schematic representation of RNA structural motifs inserted into the Δ3-5 RNA. Δ3-5/HHI- a hammerhead (HHI) ribozyme was cloned at the 3' region of Δ3-5 RNA; S3- a stable stem-loop structure was incorporated at the 3' end of the Δ3-5/HHI chimera; S5- stable stem-loop structures were incorporated at the 5' and the 3' ends of Δ3-5/HHI ribozyme chimera; S35- sequence at the 3' end of the Δ3-5/HHI ribozyme chimera was altered to enable duplex formation between the 5' end and a complementary 3' region of the same RNA; S35Plus- in addition to structural alterations of S35, sequences were altered to facilitate additional duplex formation within the non-ribozyme sequence of the Δ3-5/HHI chimera.

FIG. 4. Northern analysis to quantitate ribozyme expression in T cell lines transduced with Δ3-5 vectors. A) Δ3-5/HHI and its variants were cloned individually into the DC retroviral vector (Sullenger et al., 1990 supra). Northern analysis of ribozyme chimeras expressed in MT-2 cells was performed. Total RNA was isolated from cells (Chomczynski & Sacchi, 1987 Analytical Biochemistry 162, 156–159), and transduced with various constructs described in FIG. 3. Northern analysis was carried out using standard protocols (Curr. Protocols Mol. Biol. 1992, ed. Ausubel et al., Wiley & Sons, NY). Nomenclature is same as in FIG. 3. This assay measures the level of expression from the type 2 pol III promoter. B) Expression of S35 constructs in MT2 cells. S35 (+ribozyme), S35 construct containing HHI ribozyme. S35 (-ribozyme), S35 construct containing no ribozyme.

FIG. 5. Ribozyme activity in total RNA extracted from transduced MT-2 cells. Total RNA was isolated from cells transduced with Δ3-5 constructs described in FIG. 4. In a standard ribozyme cleavage reaction, 5 μg total RNA and trace amounts of 5' terminus-labeled ribozyme target RNA were denatured separately by heating to 90° C. for 2 min in the presence of 50 mM Tris-HCl, pH 7.5 and 10 mM $MgCl_2$. RNAs were renatured by cooling the reaction mixture to 37° C. for 10–15 min. Cleavage reaction was initiated by mixing the labeled substrate RNA and total cellular RNA at 37° C.

The reaction was allowed to proceed for ~18 h, following which the samples were resolved on a 20% urea-polyacrylamide gel. Bands were visualized by autoradiography.

FIG. 6. Ribozyme expression and activity levels in S35-transduced clonal CEM cell lines. A) Northern analysis of S35-transduced clonal CEM cell lines. Standard curve was generated by spiking known concentrations of in vitro transcribed S5 RNA into total cellular RNA isolated from non-transduced CEM cells. Pool, contains RNA from pooled cells transduced with S35 construct. Pool (-G418 for 3 Mo), contains RNA from pooled cells that were initially selected for resistance to G418 and then grown in the absence of G418 for 3 months. Lanes A through N contain RNA from individual clones that were generated from the pooled cells transduced with S35 construct. $tRNA_j^{met}$, refers to the endogenous tRNA. S35, refers to the position of the ribozyme band. M, marker lane. B) Activity levels in S35-transduced clonal CEM cell lines. RNA isolation and cleavage reactions were as described in FIG. 5. Nomenclature is same as in FIG. 6A except, S, 5' terminus-labeled substrate RNA. P, 8 nt 5' terminus-labeled ribozyme-mediated RNA cleavage product.

FIGS. 7 and 8 are proposed secondary structures of S35 and S35 containing a desired RNA (HHI), respectively. The position of HHI ribozyme is indicated in FIG. 8. Intramolecular stem refers to the stem structure formed due to an intramolecular base-paired interaction between the 3' sequence and the complementary 5' terminus. The length of the stem ranges from 15–16 base-pairs. Location of the A and the B boxes are shown.

FIGS. 9 and 10 are proposed secondary structures of S35 plus and S35 plus containing HHI ribozyme.

FIGS. 11a,b and 12a,b are the nucleotide base sequences of S35, HHIS35, S35 Plus, and HHIS35 Plus respectively.

FIG. 13 is a general formula for pol III RNA of this invention.

Figure 15A:
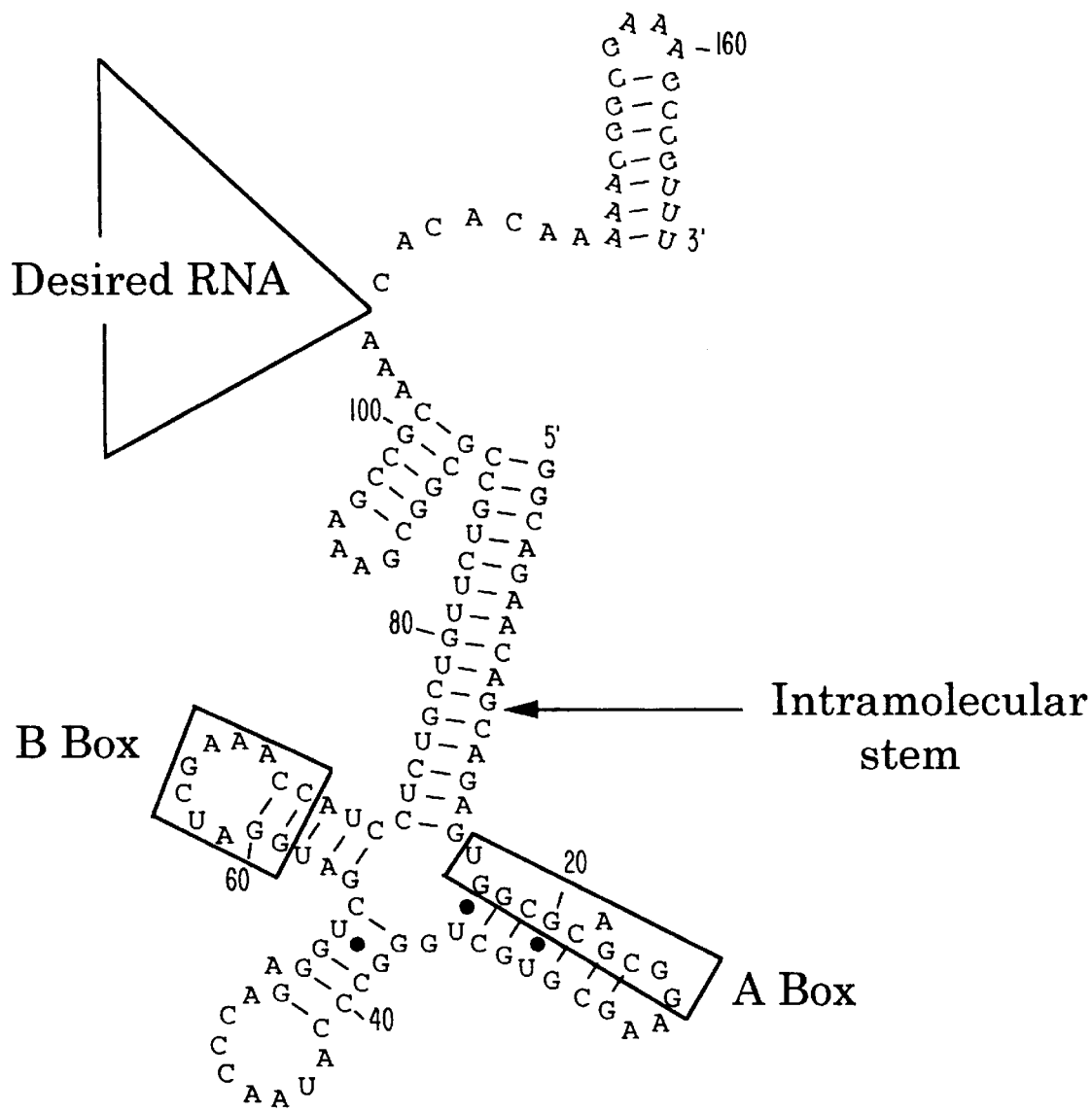

FIGS. 15A and B contain proposed secondary structures of 5T construct alone and 5T contruct containing a desired RNA (HHI ribozyme) respectively.

FIG. 16 is a diagrammatic representation of TRZ-tRNA chimeras. The site of desired RNA insertion is indicated.

FIG. 17 A shows the general structure of HHITRZ-A ribozyme chimera. A hammerhead ribozyme targeted to site I is inserted into the stem II region of TRZ-tRNA chimera. B shows the general structure of HPITRZ-A ribozyme chimera. A hairpin ribozyme targeted to site I is cloned into the indicated region of TRZ-tRNA chimera.

Figure 18:
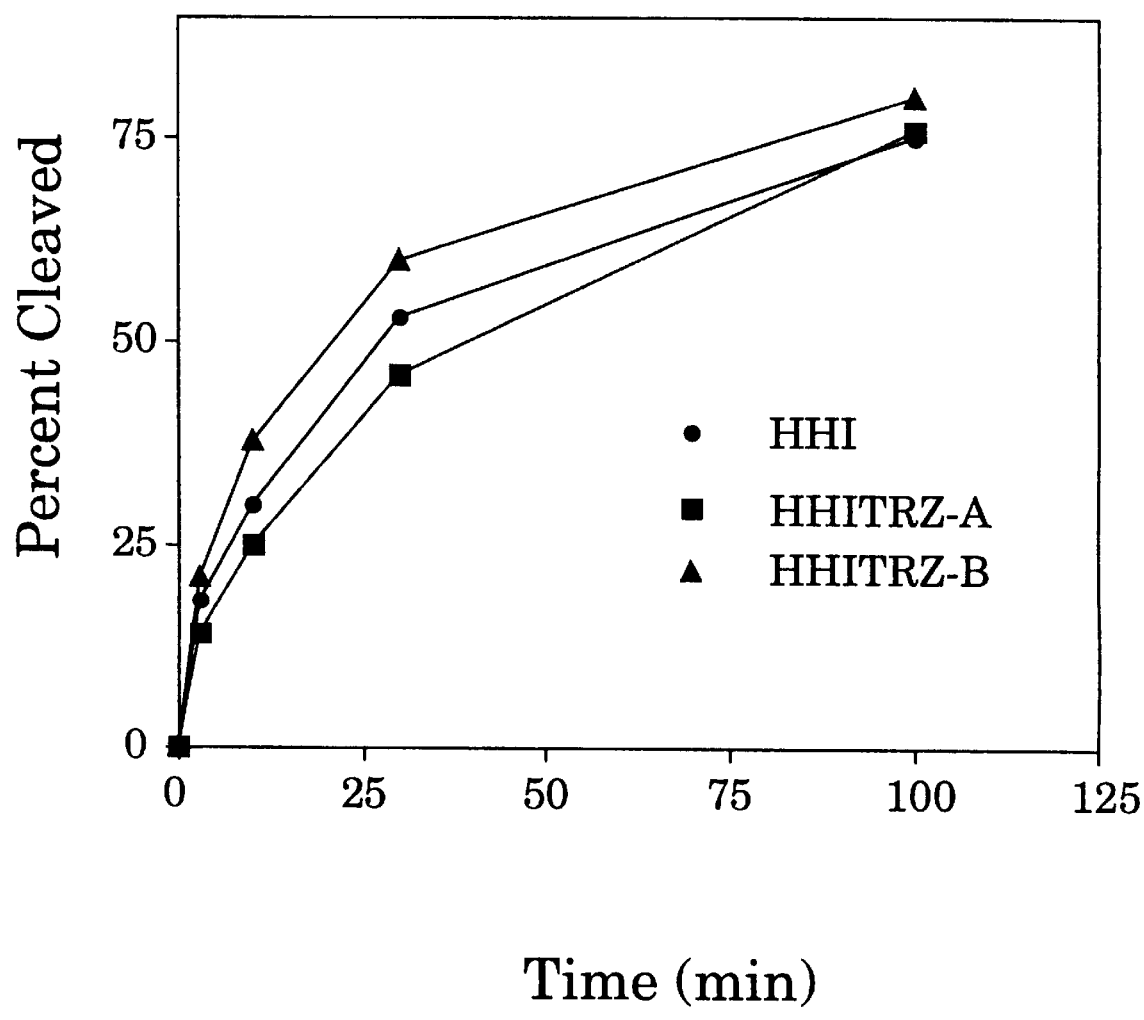

FIG. 18 shows a comparison of RNA cleavage activity of HHITRZ-A, HHITRZ-B and a chemically synthesized HHI hammerhead ribozymes.

To make internally-labeled substrate RNA for trans-ribozyme cleavage reactions, a 613 nt region (containing site I) was synthesized by PCR using primers that place the T7 RNA promoter upstream of the amplified sequence. Target RNA was transcribed, using T7 RNA polymerase, in a standard transcription buffer in the presence of [α-$^{32}$P]CTP. The reaction mixture was treated with 15 units of ribonuclease-free DNaseI, extracted with phenol followed chloroform:isoamyl alcohol (25:1), precipitated with isopropanol and washed with 70% ethanol. The dried pellet was resuspended in 20 μl DEPC-treated water and stored at -20° C.

Unlabeled ribozyme (200 nM) and internally labeled 613 nt substrate RNA (<10 nM) were denatured and renatured separately in a standard cleavage buffer (containing 50 mM Tris.HCl pH 7.5 and 10 mM MgCl$_2$) by heating to 90° C. for 2 min. and slow cooling to 37° C. for 10 min. The reaction was initiated by mixing the ribozyme and substrate mixtures and incubating at 37° C. Aliquots of 5 μl were taken at regular time intervals, quenched by adding an equal volume of 2X formamide gel loading buffer and frozen on dry ice. The samples were resolved on 5% polyacrylamide sequencing gel and results were quantitatively analyzed by radio-analytic imaging of gels with a PhosphorImager (Molecular Dynamics, Sunnyvale, Calif.).

RNA THERAPY

Few antiviral drug therapies are available that effectively inhibit established viral infections. Consequently, prophylactic immunization has become the method of choice for protection against viral pathogens. However, effective vaccines for divergent viruses such as those causing the common cold, and HIV, the etiologic agent of AIDS, may not be feasible. Consequently, new antiviral strategies are being developed for combating viral infections.

Gene therapy represents a potential alternative strategy, where antiviral genes are stably transferred into susceptible cells. Such gene therapy approaches have been termed "intracellular immunization" since cells expressing antiviral genes become immune to viral infection (Baltimore, 1988 Nature 335, 395–396). Numerous forms of antiviral genes have been developed, including protein-based antivirals such as transdominant inhibitory proteins (Malim at al., 1993 J. Exp. Med., Bevec et al., 1992 P.N.A.S. (USA) 89, 9870–9874; Bahner et al., 1993 J. Virol. 67, 3199–3207) and viral-activated suicide genes (Ashorn et al., 1990 P.N.A.S. (USA) 87, 8889–8893). Although effective in tissue culture, protein-based antivirals have the potential to be immunogenic in vivo. It is therefore conceivable that treated cells expressing such foreign antiviral proteins will be eradicated by normal immune functions. Alternatives to protein based antivirals are RNA based molecules such as antisense RNAs, decoy RNAs, agonist RNAs, antagonist RNAs, therapeutic editing RNAs and ribozymes. RNA is not immunogenic; therefore, cells expressing such therapeutic RNAs are not susceptible to immune eradication.

In order for RNA-based gene therapy approaches to be effective, sufficient amounts of the therapeutic RNA must accumulate in the appropriate intracellular compartment of the treated cells. Accumulation is a function of both promoter strength of the antiviral gene, and the intracellular stability of the antiviral RNA. Both RNA polymerase II(pol II) and RNA polymerase III (pol III) based expression systems have been used to produce therapeutic RNAs in cells (Sarver & Rossi, 1993 AIDS Res. & Human Retroviruses 9, 483–487; Yu et al., 1993 P.N.A.S.(USA) 90, 6340–6344). However, pol III based expression cassettes are theoretically more attractive for use in expressing antiviral RNAs for the following reasons. Pol II produces messenger RNAs located exclusively in the cytoplasm, whereas pol II produces functional RNAs found in both the nucleus and the cytoplasm. Pol II promoters tend to be more tissue restricted, whereas pol III genes encode tRNAs and other functional RNAs necessary for basic "housekeeping" functions in all cell types. Therefore, pol III promoters are likely to be expressed in all tissue types. Finally, pol III transcripts from a given gene accumulate to much greater levels in cells relative to pol II genes.

Intracellular accumulation of therapeutic RNAs is also dependent on the method of gene transfer used. For example, the retroviral vectors presently used to accomplish stable gene transfer, integrate randomly into the genome of target cells. This random integration leads to varied expression of the transferred gene in individual cells comprising the bulk treated cell population. Therefore, for maximum effectiveness, the transferred gene must have the capacity to express therapeutic amounts of the antiviral RNA in the entire treated cell population, regardless of the integration site.

Pol III SYSTEM

The following is just one non-limiting example of the invention. A pol III based genetic element derived from a human tRNA$_j^{met}$ gene and termed Δ3-5 (FIG. 2; Adeniyi-Jones et. al., 1984 supra), has been adapted to express antiviral RNAs (Sullenger et al., 1990 Mol Cell, Biol. 10, 6512–6523). This element was inserted into the DC retroviral vector (Sullenger et al., 1990 Mol. Cell. Biol. 10, 6512–6523) to accomplish stable gene transfer, and used to express antisense RNAs against moloney murine leukemia virus and anti-HIV decoy RNAs (Sullenger et al., 1990 Mol. Cell. Biol. 10, 6512–6523; Sullenger et al., 1990 Cell 63, 601–608; Sullenger et al., 1991 J. Virol. 65, 6811–6816; Lee et al., 1992 The New Biologist 4, 66–74). Clonal lines are expanded from individual cells present in the bulk population, and therefore express similar amounts of the therapeutic RNA in all cells. Development of a vector system that generates therapeutic levels of therapeutic RNA in all treated cells would represent a significant advancement in RNA based gene therapy modalities.

Applicant examined hammerhead (HHI) ribozyme (RNA with enzymatic activity) expression in human T cell lines using the Δ3-5 vector system (These constructs are termed "Δ3-5/HHI"; FIG. 3). On average, ribozymes were found to accumulate to less than 100 copies per cell in the bulk T cell populations. In an attempt to improve expression levels of the Δ3-5 chimera, the applicant made a series of modified Δ3-5 gene units containing enhanced promoter elements to increase transcription rates, and inserted structural elements to improve the intracellular stability of the ribozyme transcripts (FIG. 3). One of these modified gene units, termed S35, gave rise to more than a 100-fold increase in ribozyme accumulation in bulk T cell populations relative to the original Δ3-5/HHI vector system. Ribozyme accumulation in individual clonal lines from the pooled T cell populations ranged from 10 to greater than 100 fold more than those achieved with the original Δ3-5/HHI version of this vector. The S35 gene unit may be used to express other therapeutic RNAs including, but not limited to, ribozymes, antisense, decoy, therapeutic editing, agonist and antagonist RNAs. Application of the S35 gene unit would not be limited to antiviral therapies, but also to other diseases, such as cancer, in which therapeutic RNAs may be effective. The S35 gene unit may be used in the context of other vector systems besides retroviral vectors, including but not limited to, other stable gene transfer systems such as adeno-associated virus (AAV; Carter, 1992 Curr. Opin. Genet. Dev. 3, 74), as well as transient vector systems such as plasmid delivery and adenoviral vectors (Berkner, 1988 BioTechniques 6, 616–629).

As described below, the S35 vector encodes a truncated version of a tRNA wherein the 3' region of the RNA is base-paired to complementary nucleotides at the 5' terminus, which includes the 5' precursor portion that is normally processed off during tRNA maturation. Without being bound by any theory, Applicant believes this feature is important in the level of expression observed. Thus, those in the art can now design equivalent RNA molecules with such high expression levels. Below are provided examples of the methodology by which such vectors and tRNA molecules can be made.

Δ3-5 VECTORS

Figure 1:
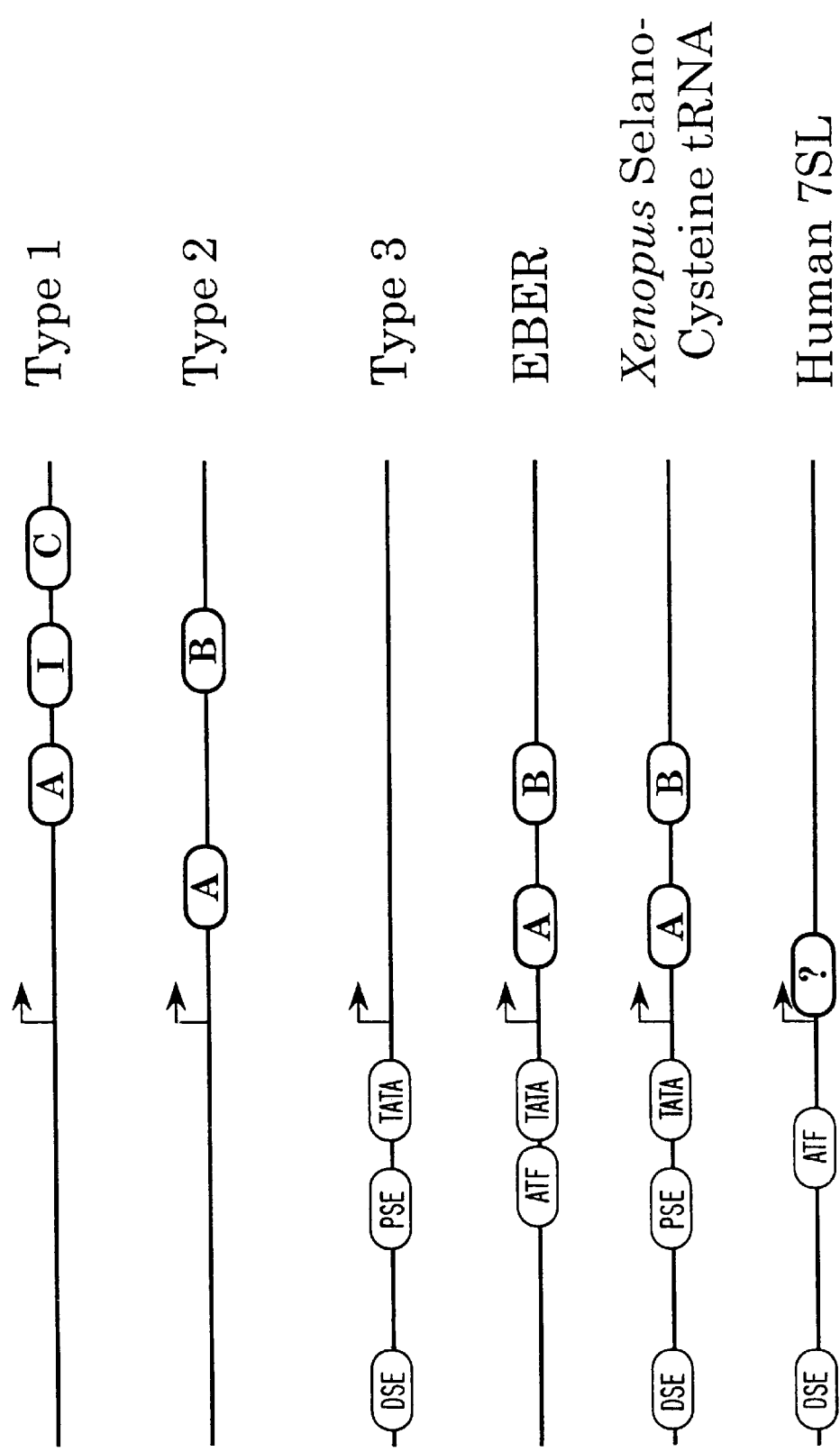
Figure 2:
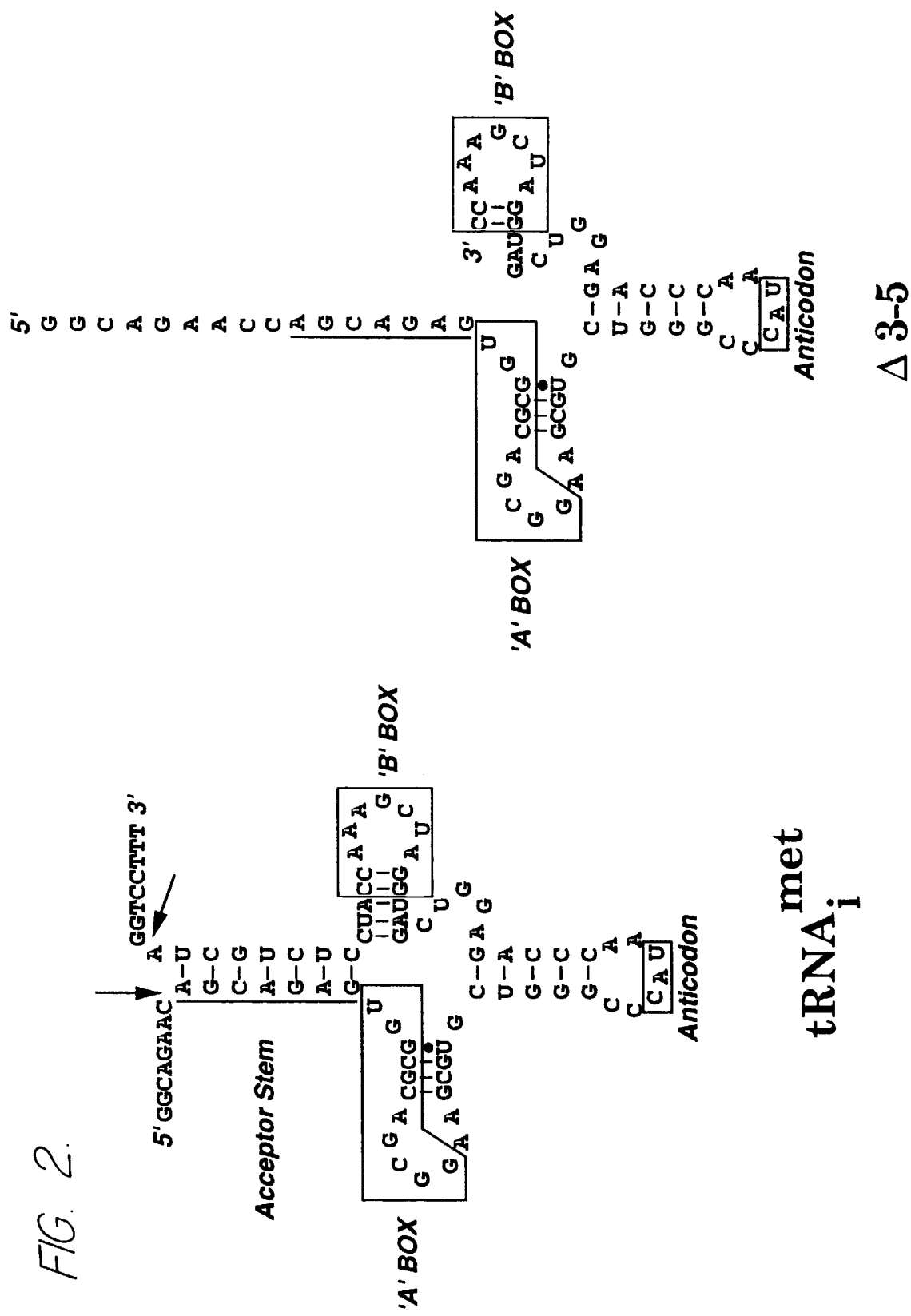

The use of a truncated human tRNA$_j^{met}$ gene, termed Δ3-5 (FIG. 2; Adeniyi-Jones at al., 1984 supra), to drive expression of antisense RNAs, and subsequently decoy RNAs (Sullenger et al., 1990 supra) has recently been reported. Because tRNA genes utilize internal pol III promoters, the antisense and decoy RNA sequences were expressed as chimeras containing tRNA$_j^{met}$ sequences. The truncated tRNA genes were placed into the U3 region of the 3' moloney murine leukemia virus vector LTR (Sullenger et al., 1990 supra).

BASE-PAIRED STRUCTURES

Figure 4A:
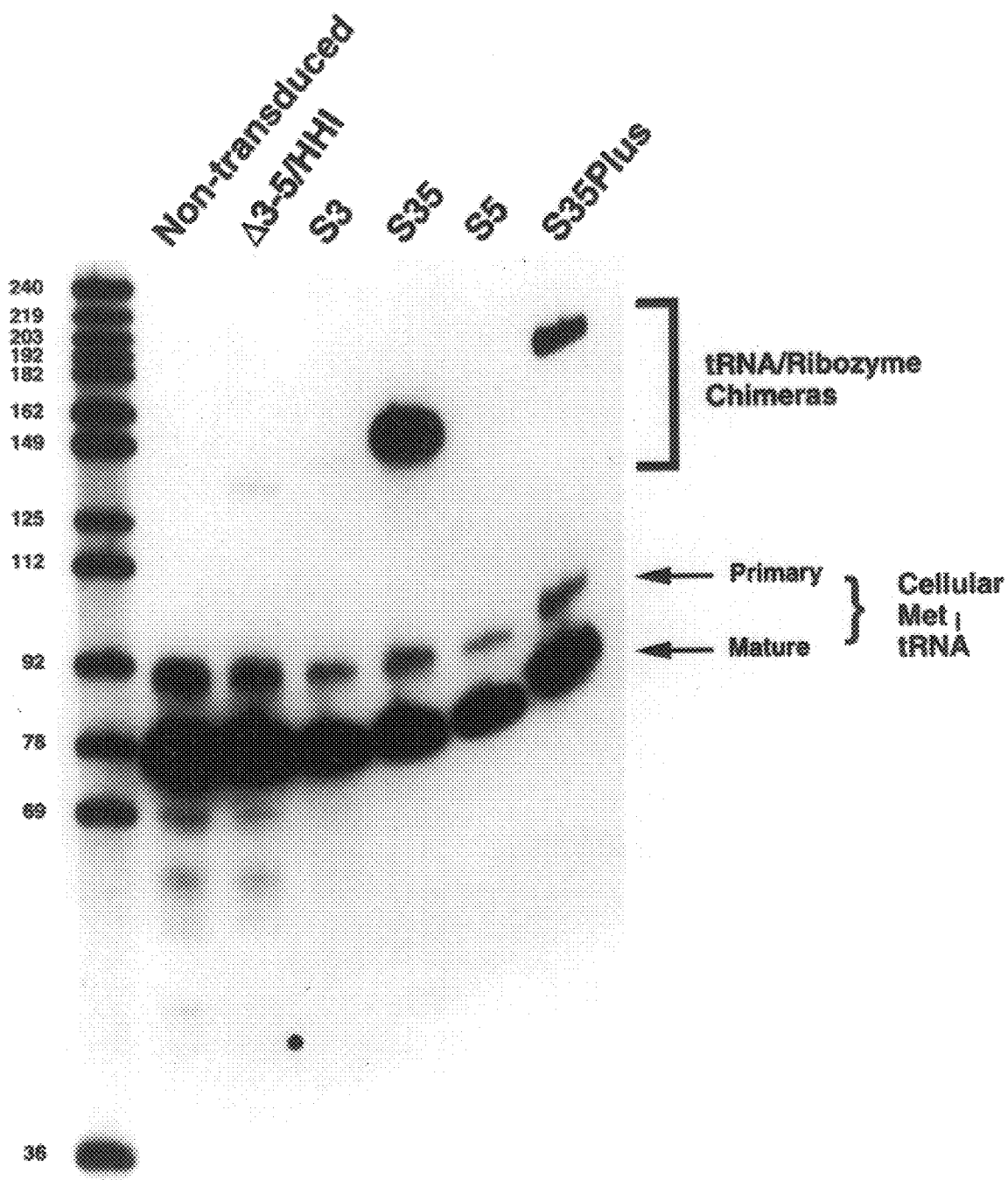

Since the Δ3-5 vector combination has been successfully used to express inhibitory levels of both antisense and decoy RNAs, applicant cloned ribozyme-encoding sequences (termed as "Δ3-5/HHI") into this vector to explore its utility for expressing therapeutic ribozymes. However, low ribozyme accumulation in human T cell lines stably transduced with this vector was observed (FIG. 4A). To try and improve accumulation of the ribozyme, applicant incorporated various RNA structural elements (FIG. 3) into one of the ribozyme chimeras (Δ3-5/HHI).

Two strategies were used to try and protect the termini of the chimeric transcripts from exonucleolytic degredation. One strategy involved the incorporation of stem-loop structures into the termini of the transcript. Two such constructs were cloned, S3 which contains a stem-loop structure at the 3' end, and S5 which contains stem-loop structures at both ends of the transcript (FIG. 3). The second strategy involved modification of the 3' terminal sequences such that the 5' terminus and the 3' end sequences can form a stable base-paired stem. Two such constructs were made: S35 in which the 3' end was altered to hybridize to the 5' leader and acceptor stem of the tRNA$_j^{met}$ domain, and S35Plus which was identical to S35 but included more extensive structure formation within the non-ribozyme portion of the Δ3-5 chimeras (FIG. 3). These stem-loop structures are also intended to sequester non-ribozyme sequences in structures that will prevent them from interfering with the catalytic activity of the ribozyme. These constructs were cloned, producer cell lines were generated, and stably-transduced human MT2 (Harada et al., 1985 supra) and CEM (Nara & Fischinger, 1988 supra) cell lines were established (Curr, Protocols Mol. Biol. 1992, ed. Ausubel et al., Wiley & Sons, NY). The RNA sequences and structure of S35 and S35 Plus are provided in FIGS. 7–12.

Figure 14:
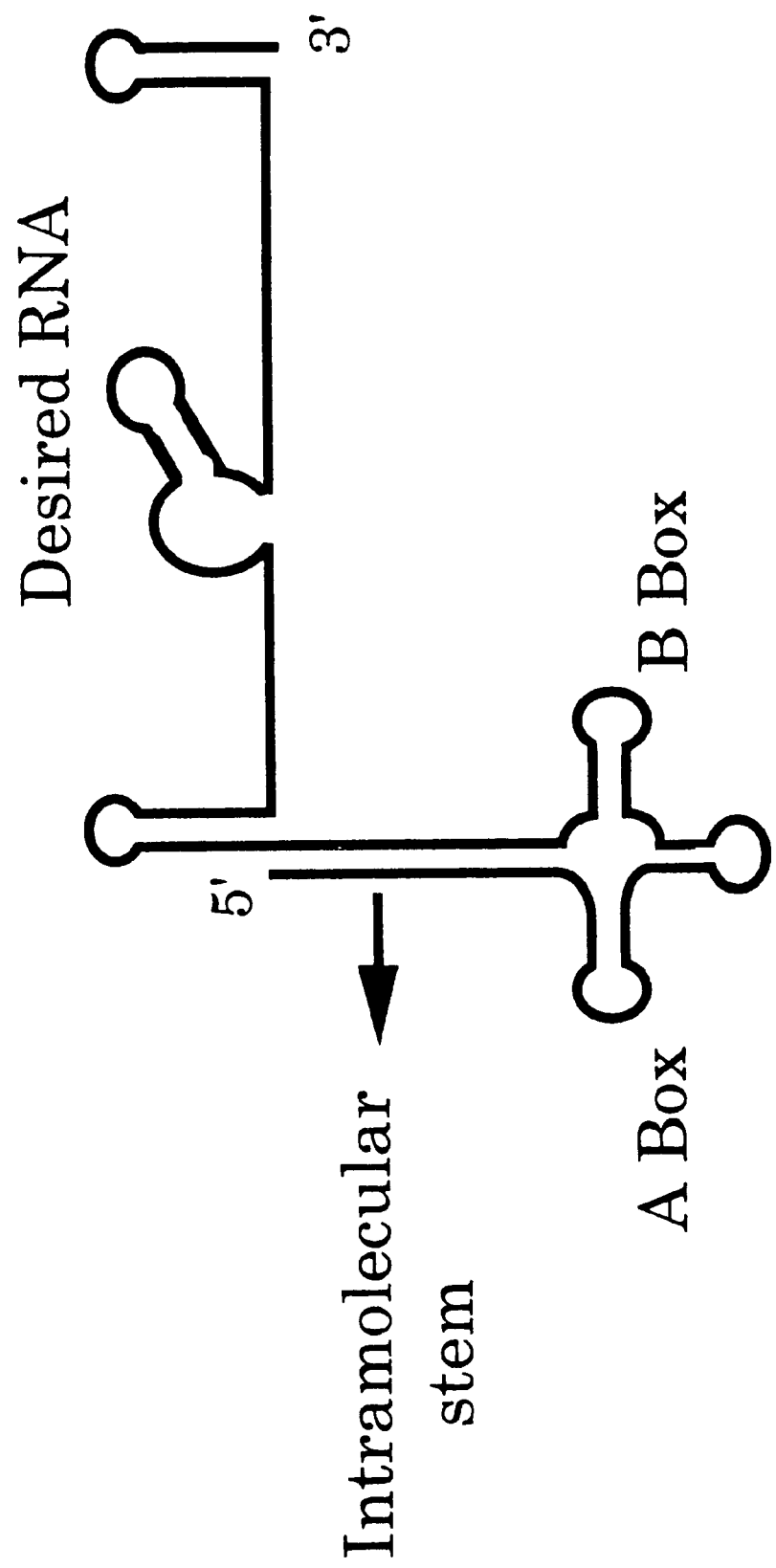
FIG. 14 is a digrammatic representation of 5T construct. In this construct the desired RNA is located 3' of the intramolecular stem.
Figure 15B:
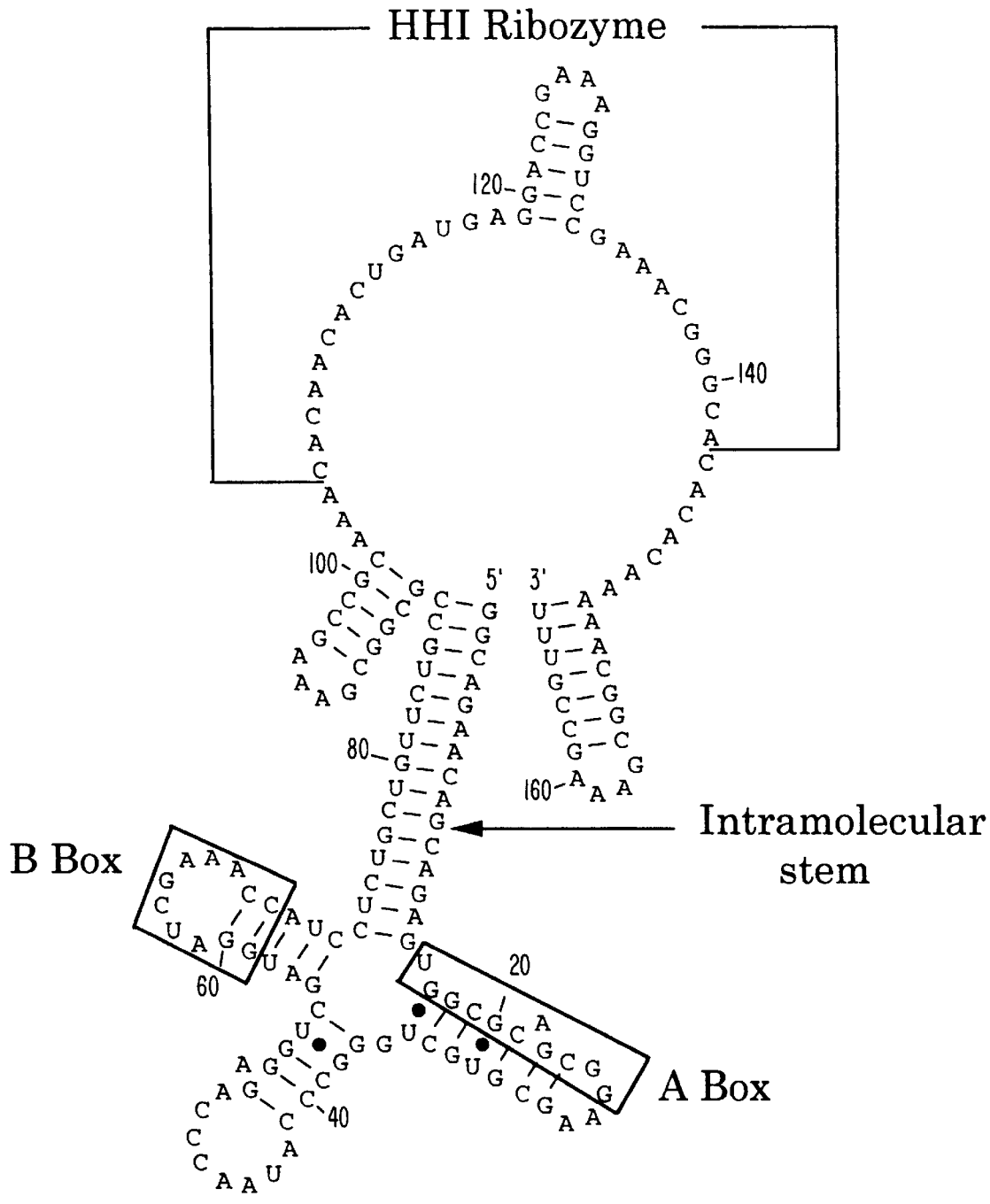

Referring to FIG. 13, there is provided a general structure for a chimeric RNA molecule of this invention. Each N independently represents none or a number of bases which may or may not be base paired. The A and B boxes are optional and can be any known A or B box, or a consensus sequence as exemplified in the figure. The desired nucleic acid to be expressed can be any location in the molecule, but preferably is on those places shown adjacent to or between the A and B boxes (designated by arrows). FIG. 14 shows one example of such a structure in which a desired RNA is provided 3' of the intramolecular stem. A specific example of such a construct is provided in FIGS. 15a and 15b.

EXAMPLE 1

Cloning of Δ3-5-Ribozyme Chimera

Oligonucleotides encoding the S35 insert that overlap by at least 15 nucleotides were designed (5' GATCCACTCT-GCTGTTCTGTTTTTGA 3' and 5' CGCGTCAAAAACA-GAACAGCAGAGTG 3'). The oligonucleotides (10 μM each) were denatured by boiling for 5 min in a buffer containing 40 mM Tris.HCl, pH8.0. The oligonucleotides were allowed to anneal by snap cooling on ice for 10–15 min.

The annealed oligonucleotide mixture was converted into a double-stranded molecule using Sequenase® enzyme (US Biochemicals) in a buffer containing 40 mM Tris.HCl, ph7.5, 20 mM MgCl$_2$, 50 mM NaCl, 0.5 mM each of the four deoxyribonucleotide triphosphates, 10 mM DTT. The reaction was allowed to proceed at 37° C. for 30 min. The reaction was stopped by heating to 70° C. for 15 min.

The double stranded DNA was digested with appropriate restriction endonucleases (BamHI and MluI) to generate ends that were suitable for cloning into the Δ3-5 vector.

The double-stranded insert DNA was ligated to the Δ3-5 vector DNA by incubating at room temperature (about 20° C.) for 60 min in a buffer containing 66 mM Tris.HCl, pH 7.6, 6.6 mM MgCl$_2$, 10 mM DTT, 0.066 μM ATP and 0.1 U/μl T4 DNA Ligase (US Biochemicals).

Competent E. coli bacterial strain was transformed with the recombinant vector DNA by mixing the cells and DNA on ice for 60 min. The mixture was heat-shocked by heating to 37° C. for 1 min. The reaction mixture was diluted with LB media and the cells were allowed to recover for 60 min at 37° C. The cells were plated on LB agar plates and incubated at 37° C. for ~18 h.

Plasmid DNA was isolated from an overnight culture of recombinant clones using standard protocols (Ausubel et al., Curr. Protocols Mol. Biology 1990, Wiley & Sons, NY).

The identity of the clones were determined by sequencing the plasmid DNA using the Sequenase® DNA sequencing kit (US Biochemicals).

The resulting recombinant Δ3-5 vector contains the S35 sequence. The HHI encoding DNA was cloned into this Δ3-5-S35 containing vector using SacII and BamHI restriction sites.

EXAMPLE 2

Northern Analysis

Figure 4B:
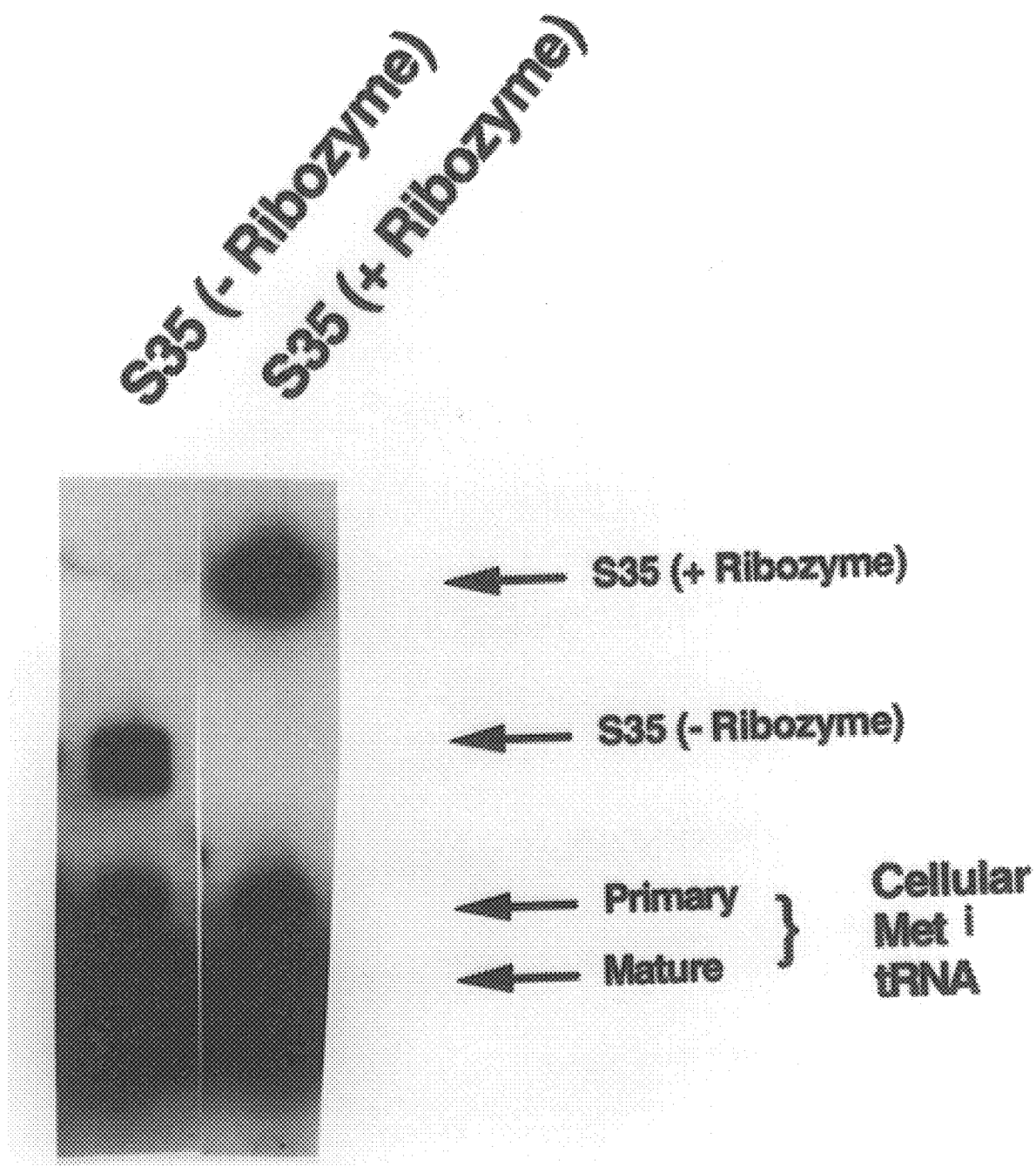

RNA from the transduced MT2 cells were extracted and the presence of Δ3-5/ribozyme chimeric transcripts were assayed by Northern analysis (Curr. Protocols Mol. Biol. 1992, ed. Ausubel et al., Wiley & Sons, NY). Northern analysis of RNA extracted from MT2 transductants showed that Δ3-5/ribozyme chimeras of appropriate sizes were expressed (FIG. 4). In addition, these results demonstrated the relative differences in accumulation among the different constructs (FIG. 4). The pattern of expression seen from the Δ3-5/HHI ribozyme chimera was similar to 12 other ribozymes cloned into the Δ3-5 vector (not shown). In MT-2 cell line, Δ3-5/HHI ribozyme chimeras accumulated, on average, to less than 100 copies per cell.

Addition of a stem-loop onto the 3' end of Δ3-5/HHI did not lead to increased Δ3-5 levels (S3 in FIG. 4). The S5 construct containing both 5' and 3' stem-loop structures also did not lead to increased ribozyme levels (FIG. 4).

Interestingly, the S35 construct expression in MT2 cells was about 100-fold more abundant relative to the original Δ3-5/HHI vector transcripts (FIG. 4). This may be due to increased stability of the S35 transcript.

EXAMPLE 3

Cleavage Activity

Figure 5:
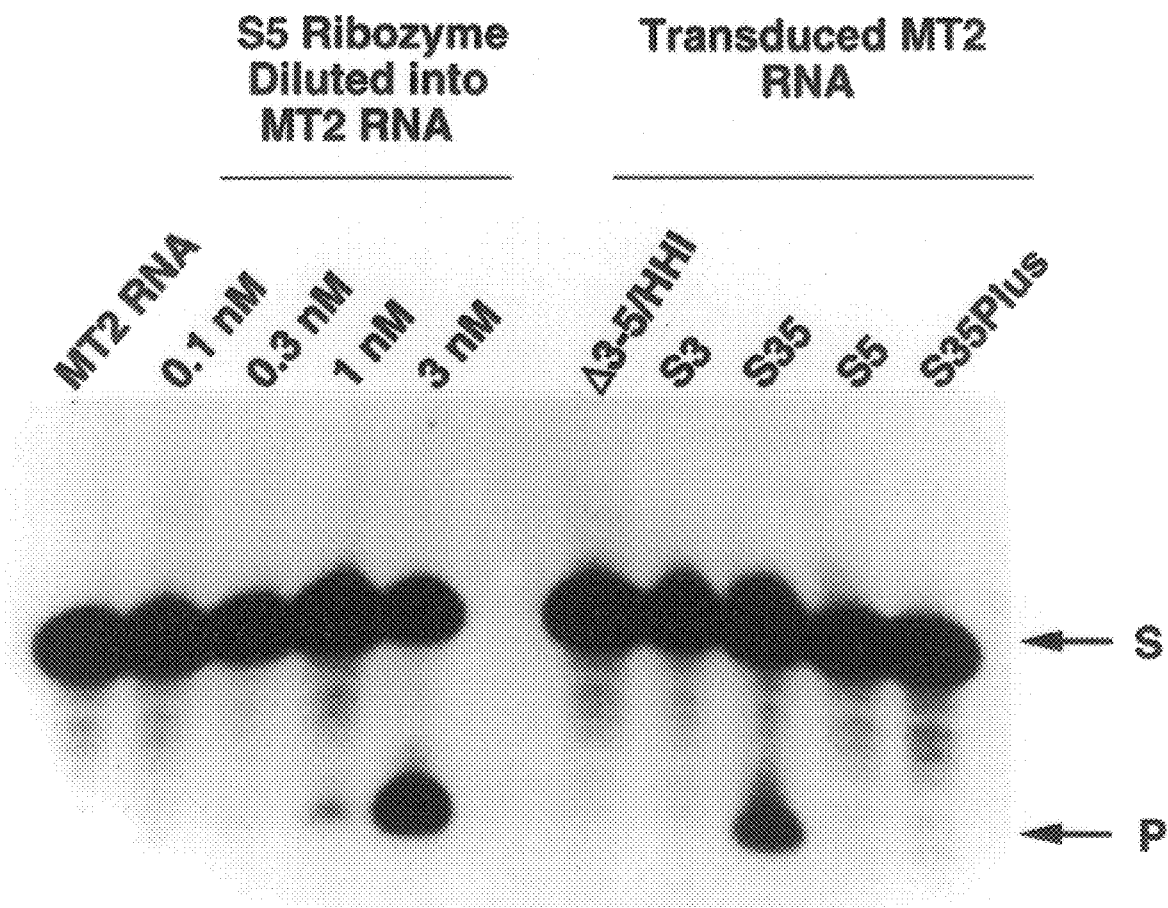

To assay whether ribozymes transcribed in the transduced cells contained cleavage activity, total RNA extracted from the transduced MT2 T cells were incubated with a labeled substrate containing the HHI cleavage site (FIG. 5). Ribozyme activity in all but the S35 constructs, was too low to detect. However, ribozyme activity was detectable in S35-transduced T cell RNA. Comparison of the activity observed in the S35-transduced MT2 RNA with that seen with MT2 RNA in which varying amounts of in vitro transcribed S5 ribozyme chimeras, indicated that between 1–3 nM of S35 ribozyme was present in S35-transduced MT2 RNA. This level of activity corresponds to an intracellular concentration of 5,000–15,000 ribozyme molecules per cell.

EXAMPLE 5

Clonal Variation

Figure 6A:
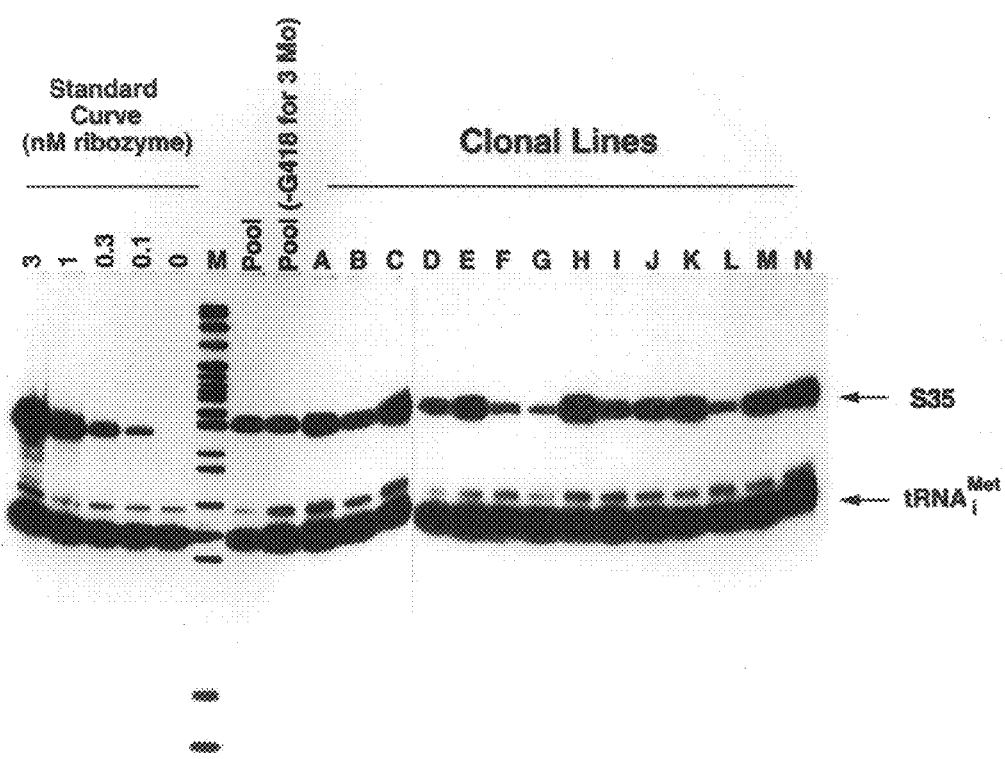
Figure 6B:
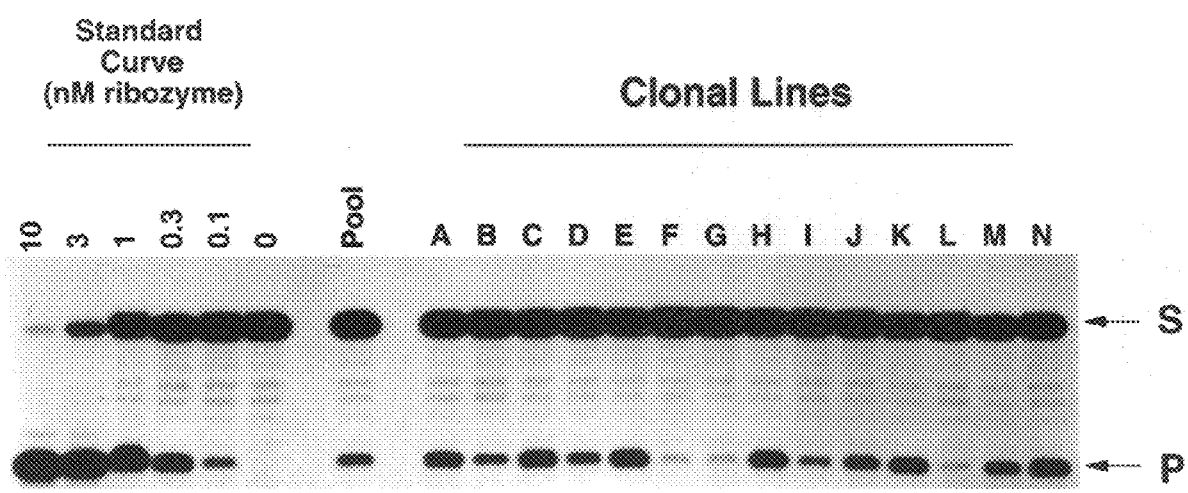
Figure 7:
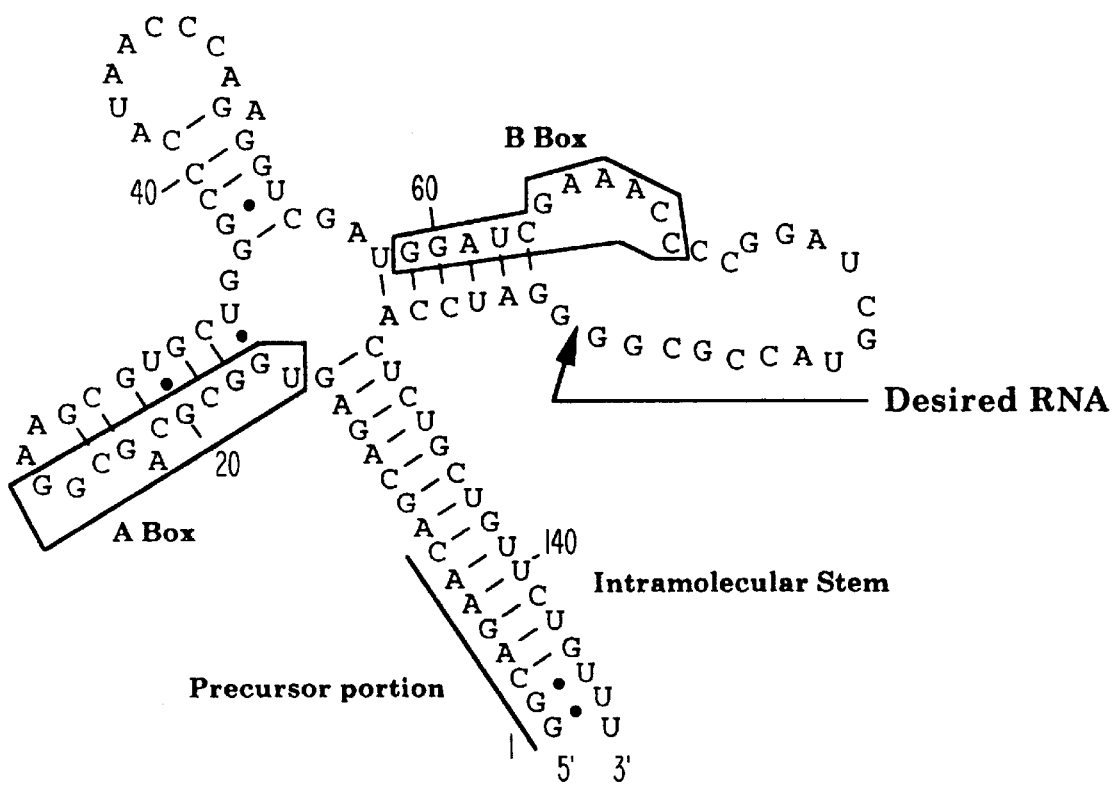
Figure 8:
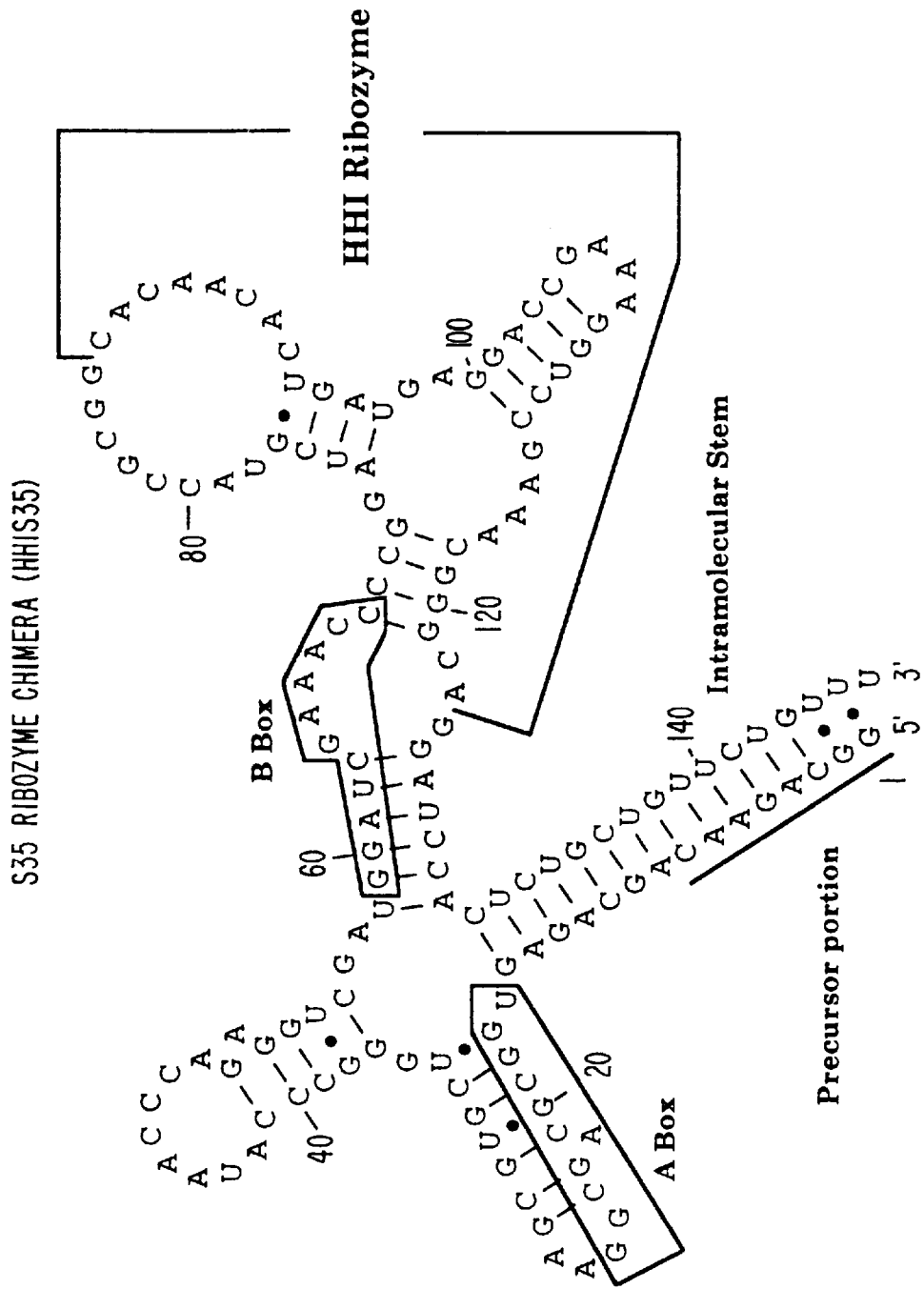
Figure 9:
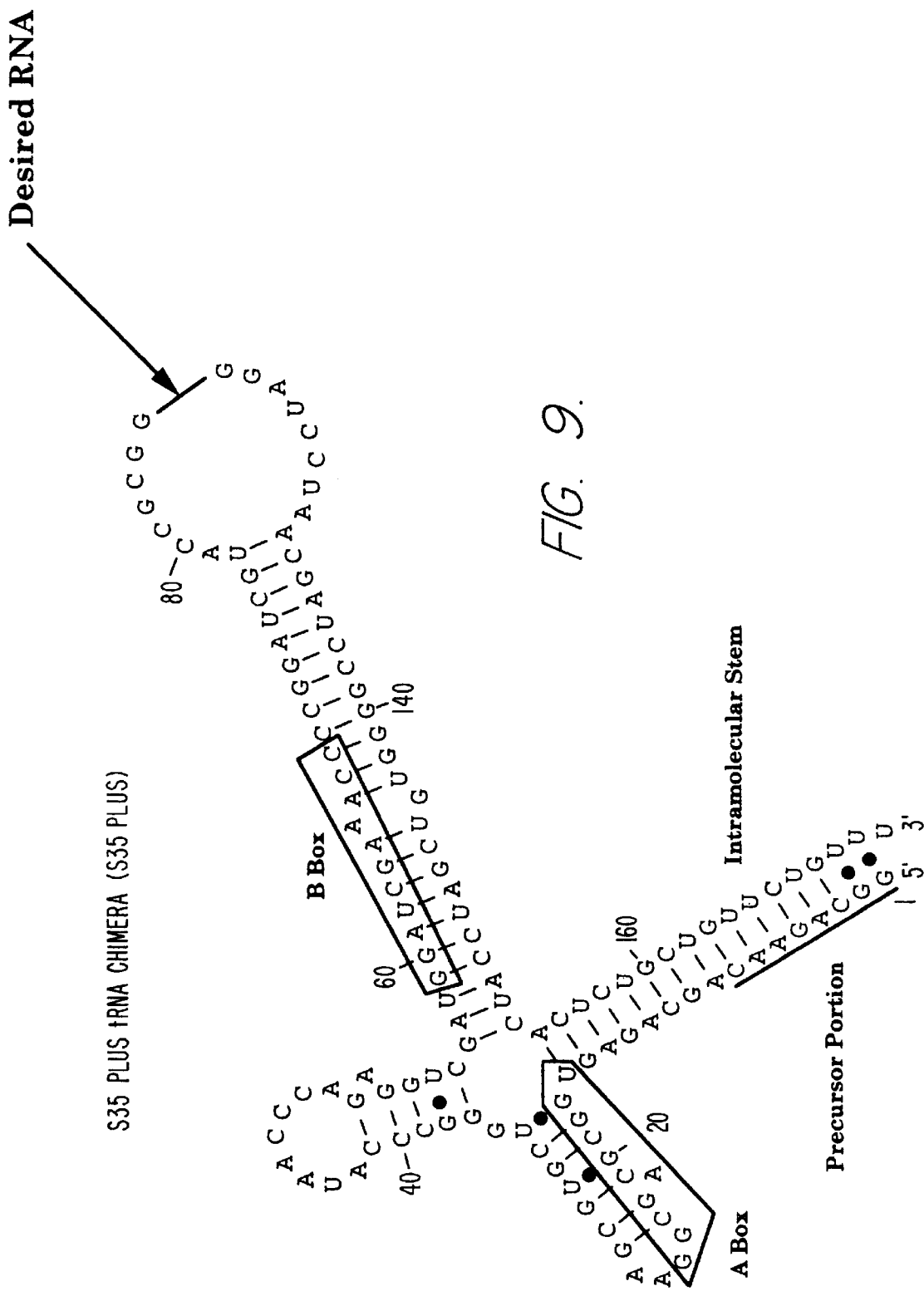
Figure 10:
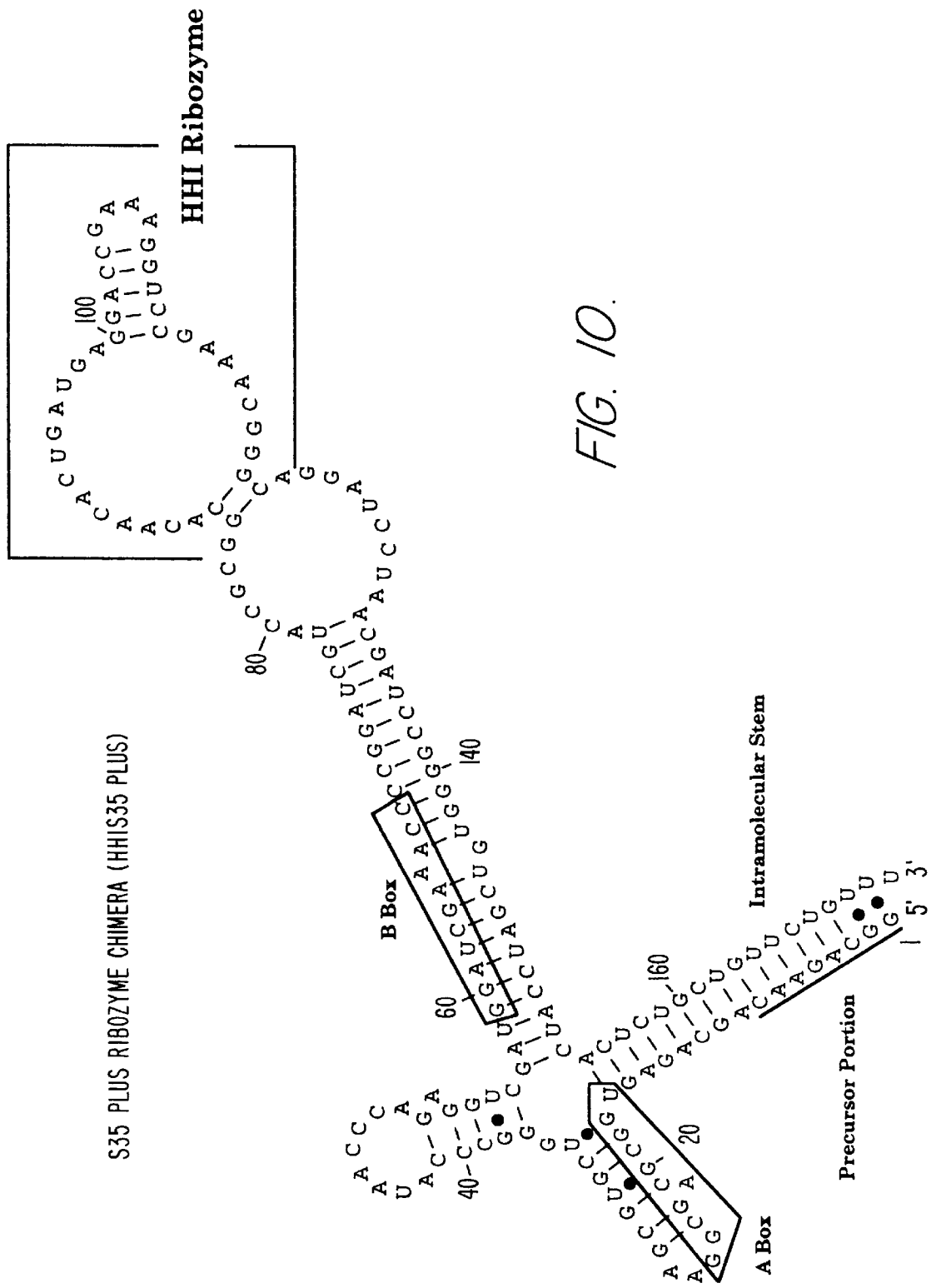

Variation in the ribozyme expression levels among cells making up the bulk population was determined by generating several clonal cell lines from the bulk S35 transduced CEM line (*Curr. Protocols Mol. Biol.* 1992, ed. Ausubel et al., Wiley & Sons, NY) and the ribozyme expression and activity levels in the individual clones were measured (FIG. 6). All the individual clones were found to express active ribozyme. The ribozyme activity detected from each clone correlated well with the relative amounts of ribozyme observed by Northern analysis. Steady state ribozyme levels among the clones ranged from approximately 1,000 molecules per cell in clone G to 11,000 molecules per cell in clone H (FIG. 6A). The mean accumulation among the clones, calculated by averaging the ribozyme levels of the clones, exactly equaled the level measured in the parent bulk population. This suggests that the individual clones are representative of the variation present in the bulk population.

The fact that all 14 clones were found to express ribozyme indicate that the percentage of cells in the bulk population expressing ribozyme is also very high. In addition, the lowest level of expression in the clones was still more than 10-fold that seen in bulk cells transduced with the original Δ3-5 vector. Therefore, the S35 gene unit should be much more effective in a gene therapy setting in which bulk cells are removed, transduced and then reintroduced back into a patient.

EXAMPLE 6

Stability

Finally, the bulk S35-transduced line, resistant to G418, was propagated for a period of 3 months (in the absence of G418) to determine if ribozyme expression was stable over extended periods of time. This situation mimicks that found in the clinic in which bulk cells are transduced and then reintroduced into the patient and allowed to propogate. There was a modest 30% reduction of ribozyme expression after 3 months. This difference probably arose from cells with varying amount of ribozyme expression and exhibiting different growth rates in the culture becoming slightly more prevalent in the culture. However, ribozyme expression is apparently stable for at least this period of time.

EXAMPLE 7

Design and Construction of TRZ-tRNA Chimera

A transcription unit, termed TRZ, is designed that contains the S35 motif (FIG. 16). A desired RNA (e.g. ribozyme) can be inserted into the indicated region of TRZ tRNA chimera. This construct might provide additional stability to the desired RNA. TRZ-A and TRZ-B are non-limiting examples of the TRZ-tRNA chimera.

Figure 17A:
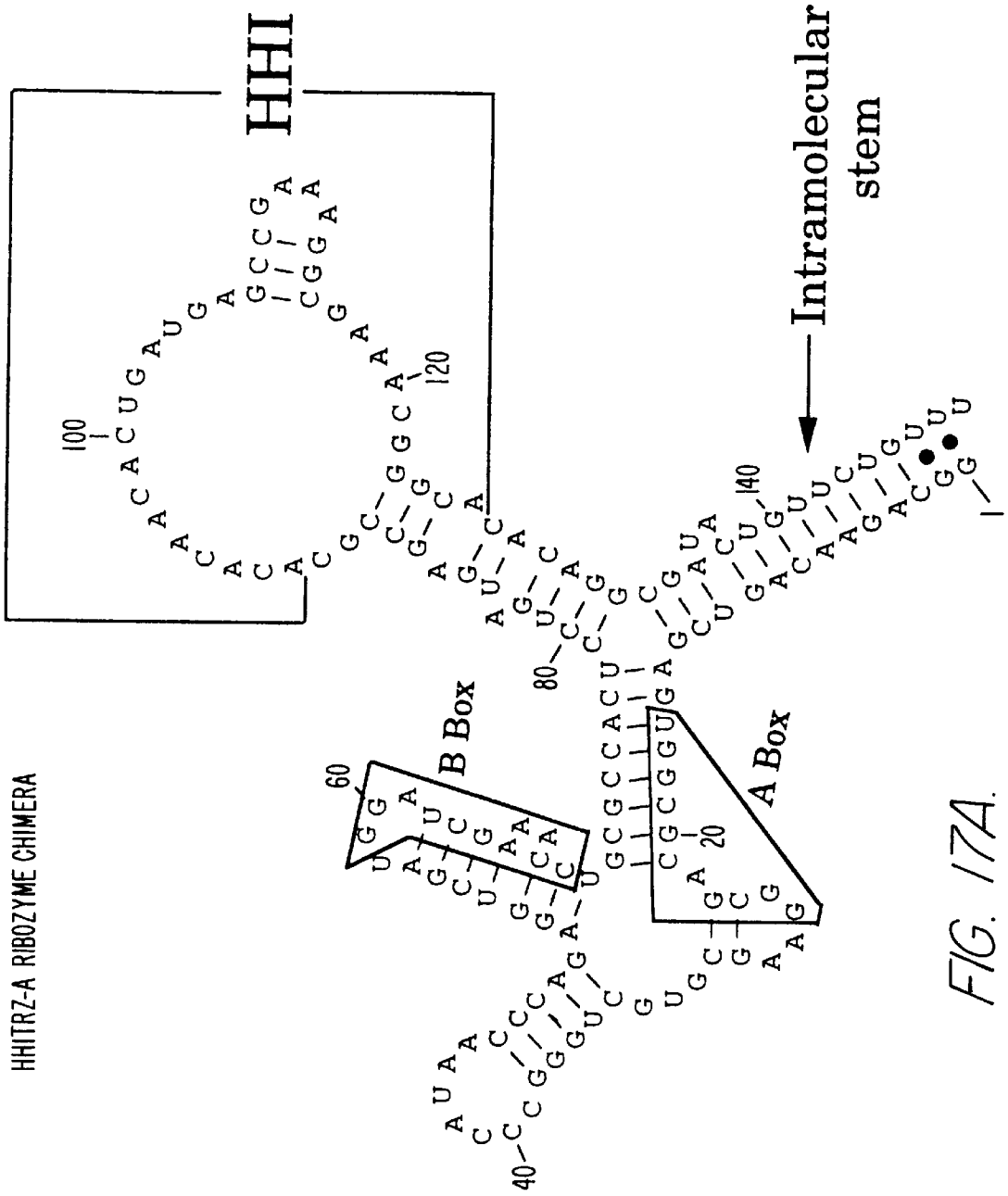
Figure 17B:
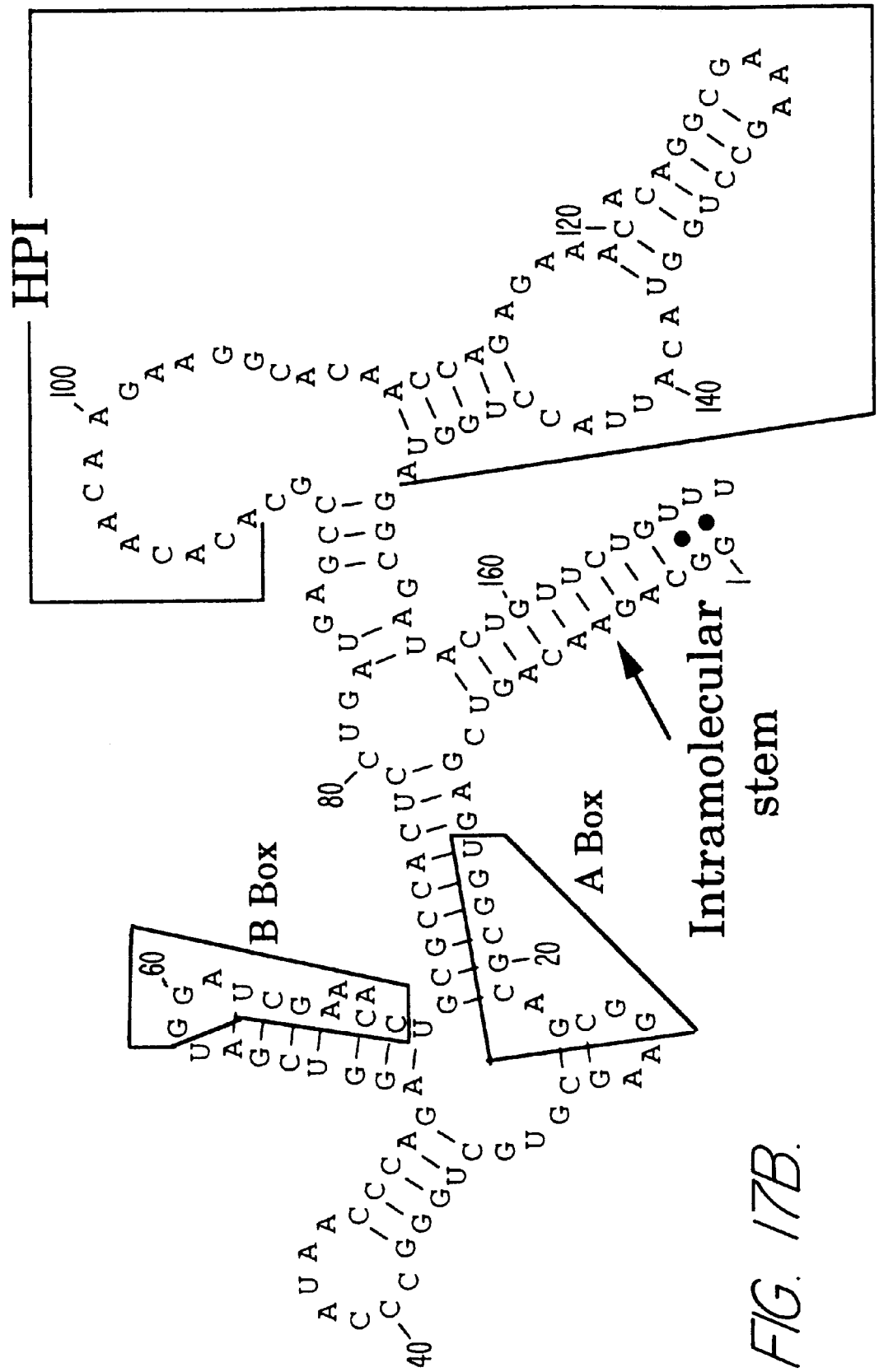

Referring to FIG. 17, a hammerhead ribozyme targeted to site I (HHITRZ-A; FIG. 17A) and a hairpin ribozyme (HPITRZ-A; FIG. 17B), also targeted to site I, is cloned individually into the indicated region of TRZ tRNA chimera. The resulting ribozyme transcripts retain full RNA cleavage activity (see for example FIG. 18). Applicant has shown that efficient expression of these TRZ tRNA chimera can be achieved in mammalian cells.

Besides ribozymes, desired RNAs like antisense, therapeutic editing RNAs, decoys, can be readily inserted into the indicated region of TRZ-tRNA chimera to achieve therapeutic levels of RNA expression in mammalian cells.

Sequences listed in FIGS. 7–12 and 15–17 are meant to be non-limiting examples. Those skilled in the art will recognize that variants (mutations, insertions and deletions) of the above examples can be readily generated using techniques known in the art, are within the scope of the present invention.

METHOD FOR ADMINISTRATION AND USE

References cited herein, as well as Draper WO 93/23569, 94/02495, 94/06331, Sullenger WO 93/12657, Thompson WO 93/04573, and Sullivan WO 94/04609, and 93/11253 describe methods for use of vectors decribed herein, and are incorporated by reference herein. In particular these vectors are useful for administration of antisense and decoy RNA molecules.

Other embodiments are within the following claims.

I claim:

1. A non-naturally occurring RNA molecule having the formula:

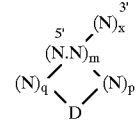

Wherein, N is independently a ribonucleotide which may be same or different, • indicates hydrogen bond formation between adjacent nucleotides, m is an image which is greater than or equal to 8; p is an integer which is greater then or equal to 1 if $(N)_p$ is present; q is an integer which is greater than or equal to 1 if $(N)_q$ is present, x is an integer which is 0 or 1; and is a desired RNA.

2. A non-naturally occurring RNA molecule having the formula:

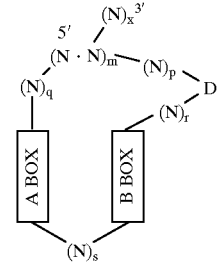

Wherein, N is independently a ribonucleotide which may be same or different, • indicates hydrogen bond formulation between adjacent nucleotides; m is an integer which is greater than or equal to 8; p is an integer which is greater than or equal to 1 if (N)$_p$ is present; q is an integer which is greater than or equal to 1 if (N)$_q$ is present; r is an integer which is greater than or equal to 1 if (N)$_r$ is present; s is an integer which is greater than or equal to 5; x is an integer which is 0 or 1; and D is a desired RNA.

3. A non-naturally RNA molecule having the formula;

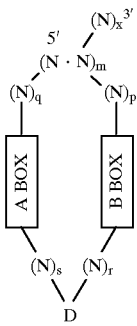

Wherein, N is independently a ribonucleotide which may be same or different; • indicates hydrogen bond formation between adjacent nucleotides; A BOX represents RNA polymerase III type 2 consensus sequence; B BOX represents RNA polymerase III type 2 consensus sequence; m is an integer which is greater than or equal to 8; p is an integer which is greater than or equal to 1 if (N)$_p$ is present; q is an integer which is greater than or equal to 1 if (N)$_q$ is present; r is an integer which is greater than or equal to 1 if (N)$_r$ is present; s is an integer which is greater than or equal to 1 (N)$_s$ is present; x is an integer which is 0 or 1; an D is a desired RNA.

4. A non-naturally occurring RNA molecule having the formula:

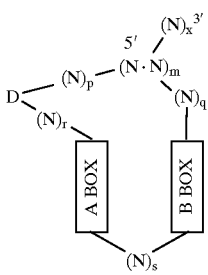

Wherein, N is independently a ribonucleotide which may be same or different; • indicates hydrogen bond formation between adjacent nucleotides; A BOX represents RNA polymerase III type 2 consensus sequence; B BOX represents RNA polymerase III type 2 consensus sequence; m is an integer which is greater than or equal to 8; p is an integer which is greater than or equal to 1 if (N)$_p$ is present; q is an integer which is greater than or equal to 1 if (N)$_q$ is present; r is an integer which is greater than or equal to 1 if (N)$_r$ is present s is an integer which is greater than or equal to 5; x is an integer which is 0 or 1; and D is a desired RNA.

5. A non-naturally occuring RNA molecule having the formula:

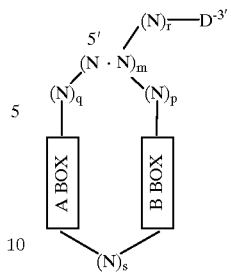

Wherein, N is independently a ribonucleotide which may be same or different; • indicates hydrogen bond formation between adjacent nucleotides; A BOX represents RNA polymerase III type 2 consensus sequence; B BOX represents RNA polymerase III type 2 consensus sequence; m is an integer which is greater than or equal to 8; p is an integer which is greater than or equal to 1 if (N)$_p$ is present; q is an integer which is greater than or equal to 1 if (N)$_q$ is present; r is an integer which is greater than or equal to 1 if (N)$_q$ is present; s is an integer which is greater than or equal to 5; and D is a desired RNA.

6. The RNA molecule of any of claims 3, 4 or 5, wherein said A BOX has the sequence 5'-URGCNNAGYGG-3', wherein R is a purine residue, N is a ribonucleotide, and Y is a pyrimidine residue; and wherein said B BOX has the sequence GGUUCGANUCC, wherein N is a ribonucleotide.

7. The RNA molecule of any of claims 1–5, wherein said desired RNA is an enzymatic RNA molecule.

8. The RNA molecule of claim 7, wherein said enzymatic RNA molecule is in a hammerhead configuration.

9. The RNA molecule of claim 7, wherein said enzymatic RNA molecule is in a hairpin configuration.

10. The RNA molecule of claim 7, wherein said enzymatic RNA molecule is in a group I ribozyme, group II ribozyme, VS ribozyme, hepatitis delta virus ribozyme or RNase P ribozyme configuration.

11. The RNA molecule of any of claims 1–5, wherein said molecule is transcribed by a RNA polymerase III based promoter system.

12. The RNA molecule of any of claims 1–5, wherein said molecule is transcribed by a type 2 RNA polymerase III promoter system.

13. The RNA molecule of any of claims 1–5, wherein, said molecule is a chimeric tRNA.

14. The RNA molecule of claim 12, wherein the A and the B boxes of said type 2 RNA polymerase III promoter, is separated by between 5 and 300 bases.

15. The RNA molecule of claim 12, wherein said desired RNA molecule includes the B box of said type 2 RNA polymerase III promoter.

16. The RNA molecule of any of claims 1–5, wherein said desired RNA molecule is selected from the group consisting of antisense RNA, decoy RNA, therapeutic editing RNA, enzymatic RNA, agonist RNA and antagonist RNA.

17. The RNA molecule of any of claims 1–5, wherein said m is greater than or equal to 12.

18. The RNA-molecule of claim 1, wherein m is greater than or equal to 15.

19. A DNA vector encoding the RNA molecule of any of claims 1–5.

20. A RNA vector encoding the RNA molecule of any of claims 1–5.

21. The vector of claim 19, wherein the portions of the vector encoding said RNA molecule function as a RNA pol III promoter.

22. A Cell comprising the vector of claim 19.
23. A Cell comprising the vector of claim 4.
24. A Cell comprising the RNA of any of claims 1–5.

* * * * *

UNITED STATES PATENT AND TRADEMARK OFFICE
CERTIFICATE OF CORRECTION

PATENT NO. : 5,902,880
DATED : May 11, 1999
INVENTOR(S) : James Thompson

It is certified that error appears in the above-identified patent and that said Letters Patent is hereby corrected as shown below:

Column 14, Line 45: delete "image" and insert --integer--

Column 14, Line 49: insert --D-- after and.

Column 14, Line 66: delete "formulation" and insert --formation--

Column 16, Line 22: delete "$(N)_q$" and insert --$(N)_r$--

Signed and Sealed this

Fourth Day of January, 2000

Attest:

Attesting Officer

*Acting Commissioner of Patents and Trademarks*